(12) United States Patent
Gross

(10) Patent No.: US 11,013,906 B2
(45) Date of Patent: May 25, 2021

(54) RECIPROCATING INTRAVASCULAR BLOOD PUMP

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 98 days.

(21) Appl. No.: 16/399,101

(22) Filed: Apr. 30, 2019

(65) Prior Publication Data

US 2019/0255236 A1     Aug. 22, 2019

Related U.S. Application Data

(63) Continuation-in-part of application No. 15/831,973, filed on Dec. 5, 2017, now Pat. No. 10,568,999.

(51) Int. Cl.
| | |
|---|---|
| *A61M 60/148* | (2021.01) |
| *A61M 60/40* | (2021.01) |
| *A61M 60/50* | (2021.01) |
| *A61M 60/135* | (2021.01) |
| A61M 60/268 | (2021.01) |
| A61M 60/562 | (2021.01) |

(52) U.S. Cl.
CPC ........ *A61M 60/148* (2021.01); *A61M 60/135* (2021.01); *A61M 60/40* (2021.01); *A61M 60/50* (2021.01); A61M 60/268 (2021.01); A61M 60/562 (2021.01); A61M 2205/3334 (2013.01); A61M 2230/04 (2013.01)

(58) Field of Classification Search
CPC ..... A61M 1/122; A61M 1/125; A61M 1/1037
See application file for complete search history.

(56) References Cited

U.S. PATENT DOCUMENTS

| | | | |
|---|---|---|---|
| 5,484,385 | A | 1/1996 | Rishton |
| 5,693,091 | A | 12/1997 | Larson, Jr. et al. |
| 5,762,599 | A | 6/1998 | Sohn |
| 6,290,641 | B1 | 9/2001 | Nigroni et al. |
| 7,468,050 | B1 | 12/2008 | Kantrowitz |
| 7,544,160 | B2 | 6/2009 | Gross |
| 7,722,568 | B2 | 5/2010 | Lenker et al. |

(Continued)

OTHER PUBLICATIONS

European Search Report dated Dec. 19, 2019 which issued during the prosecution of Applicant's European App No. 19178111.1.

(Continued)

*Primary Examiner* — Suba Ganesan
(74) *Attorney, Agent, or Firm* — Sughrue Mion, PLLC

(57) ABSTRACT

Apparatus is provided that is configured to be deployed in a lumen of a blood vessel of a subject. The apparatus includes a pump portion, including an anchor configured to engage a wall of the blood vessel in order to maintain the apparatus in place within the blood vessel, and a reciprocating valve coupled to the anchor and including a set of one or more leaflets. A valve driver is configured to drive the reciprocating valve in a reciprocating pattern between (i) a first state in which the leaflets are in an open configuration allowing blood flow through the reciprocating valve, and (ii) a second state in which the leaflets are in a closed configuration inhibiting blood flow through the reciprocating valve. Other embodiments are also described.

23 Claims, 11 Drawing Sheets

(56) References Cited

U.S. PATENT DOCUMENTS

| | | |
|---|---|---|
| 7,976,452 B2 | 7/2011 | Kantrowitz |
| 8,900,191 B2 | 12/2014 | Lenker et al. |
| 2003/0032853 A1 | 2/2003 | Korakianitis et al. |
| 2016/0206798 A1* | 7/2016 | Williams ............ A61M 1/1086 |
| 2018/0326132 A1 | 11/2018 | Maimon et al. |
| 2019/0167877 A1 | 6/2019 | Gross |

OTHER PUBLICATIONS

An Office Action dated Jun. 27, 2019, which issued during the prosecution of U.S. Appl. No. 15/831,973.
Notice of Allowance dated Oct. 9, 2019, which issued during the prosecution of U.S. Appl. No. 15/831,973.

* cited by examiner

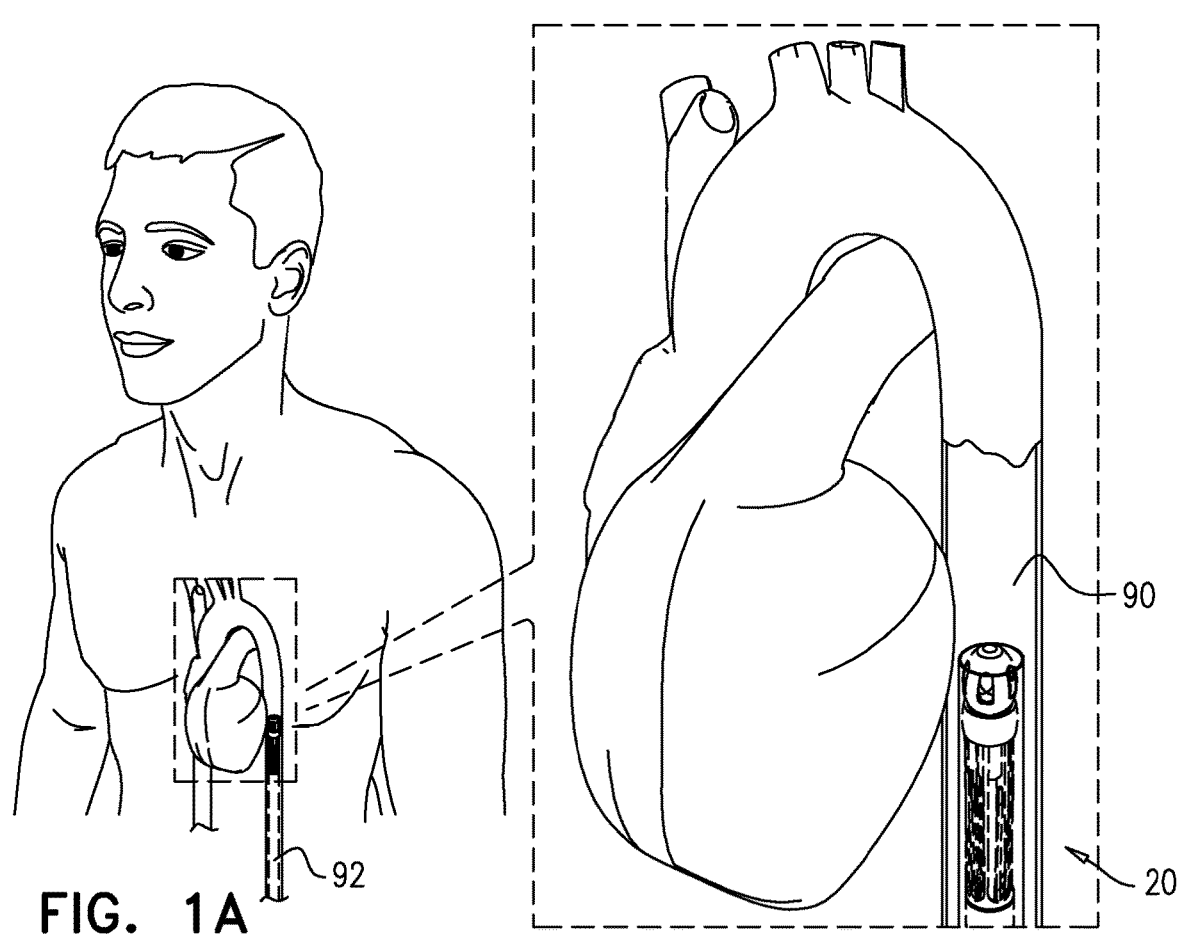
FIG. 1A
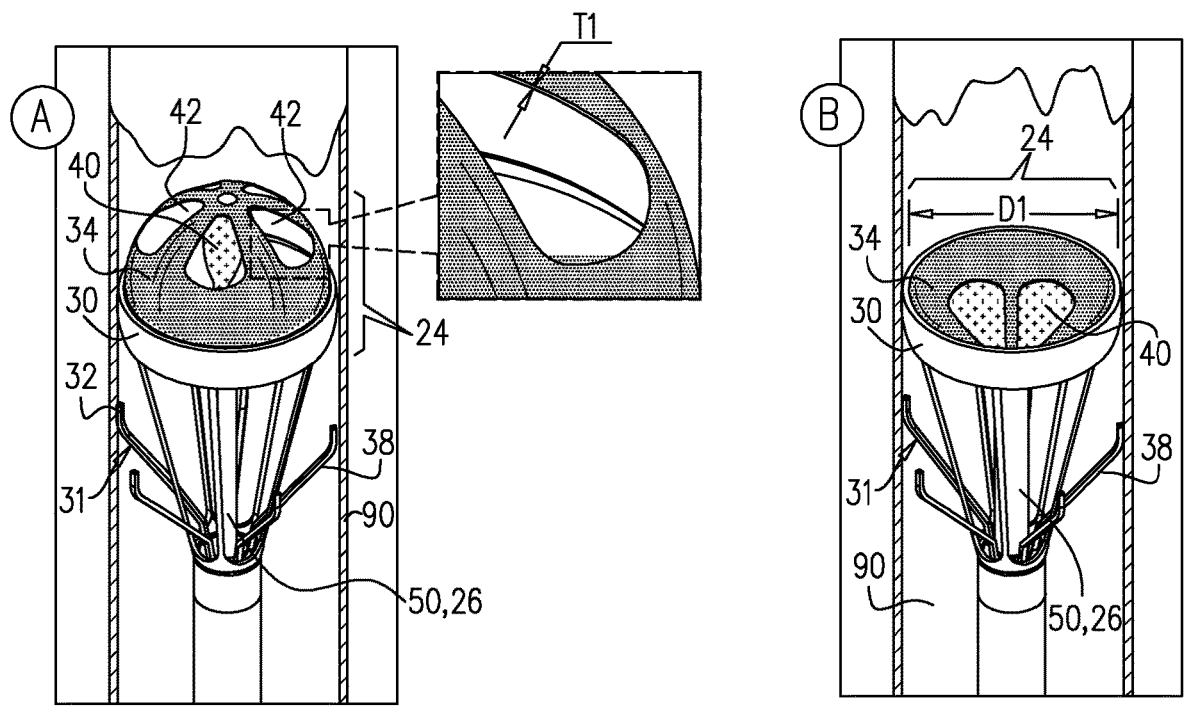
FIG. 1B
FIG. 1C

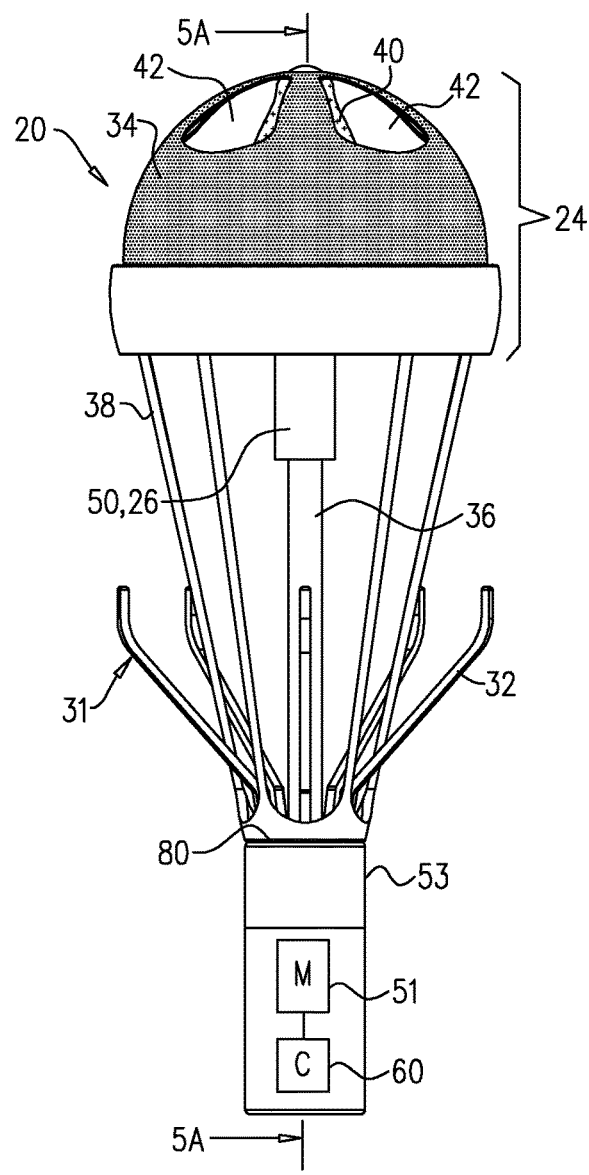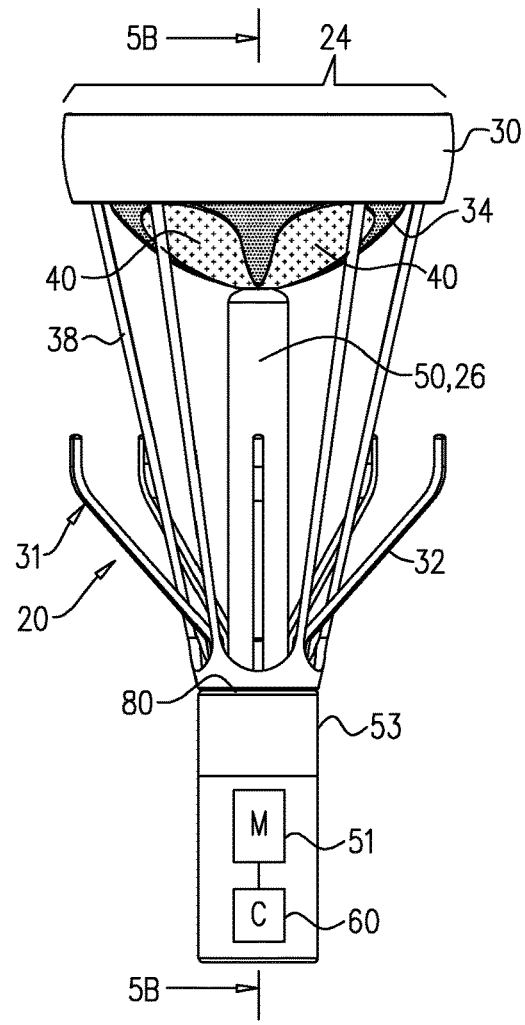
FIG. 2A  FIG. 2B
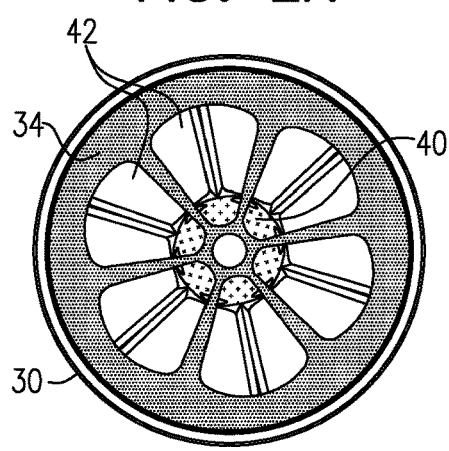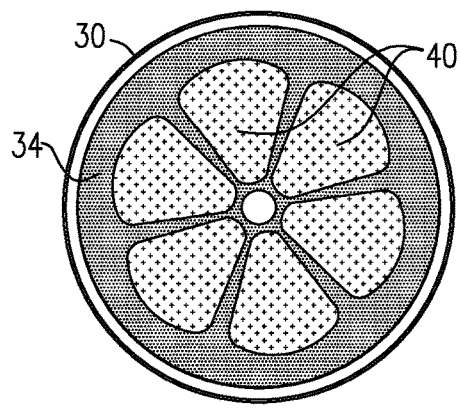
FIG. 3A  FIG. 3B

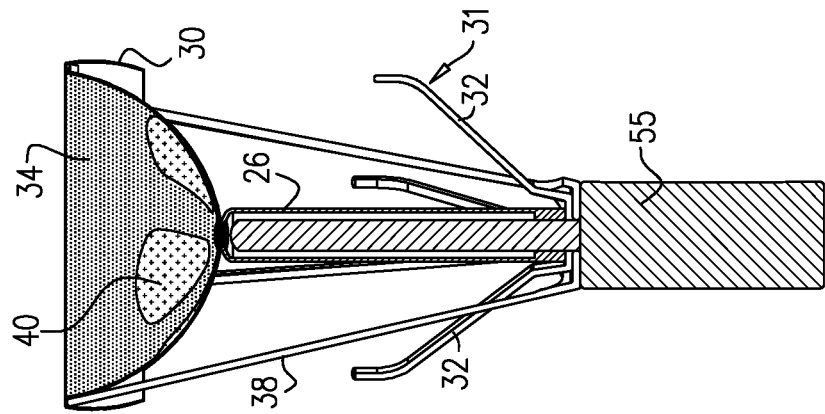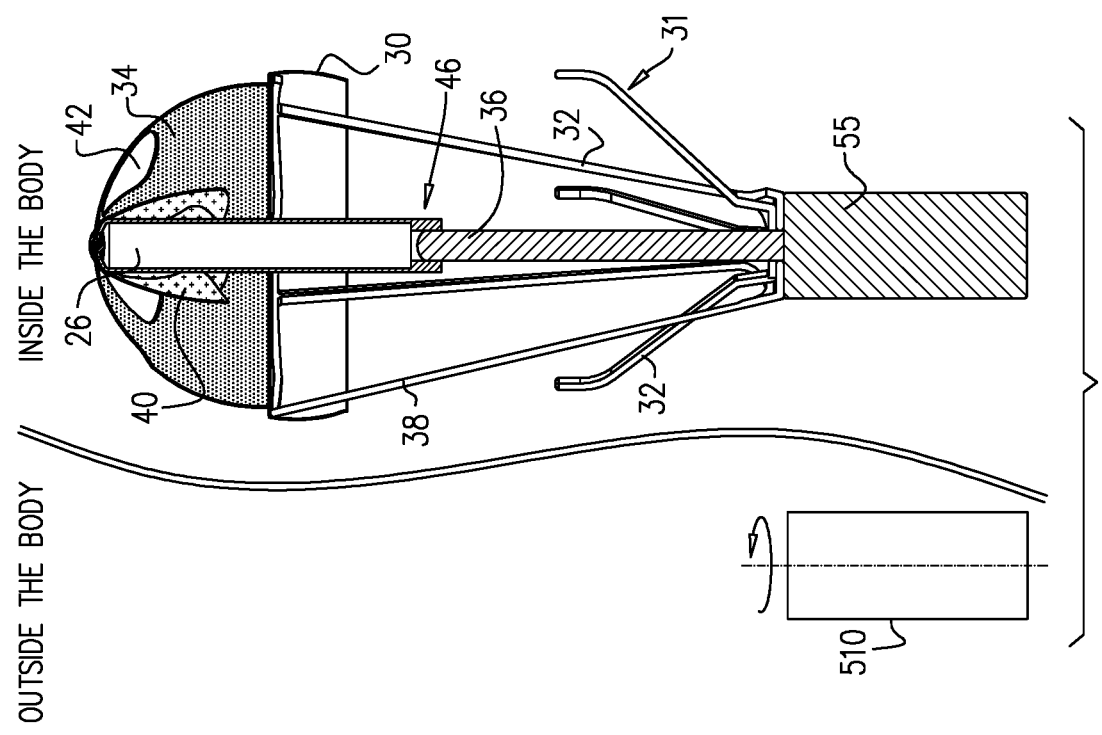

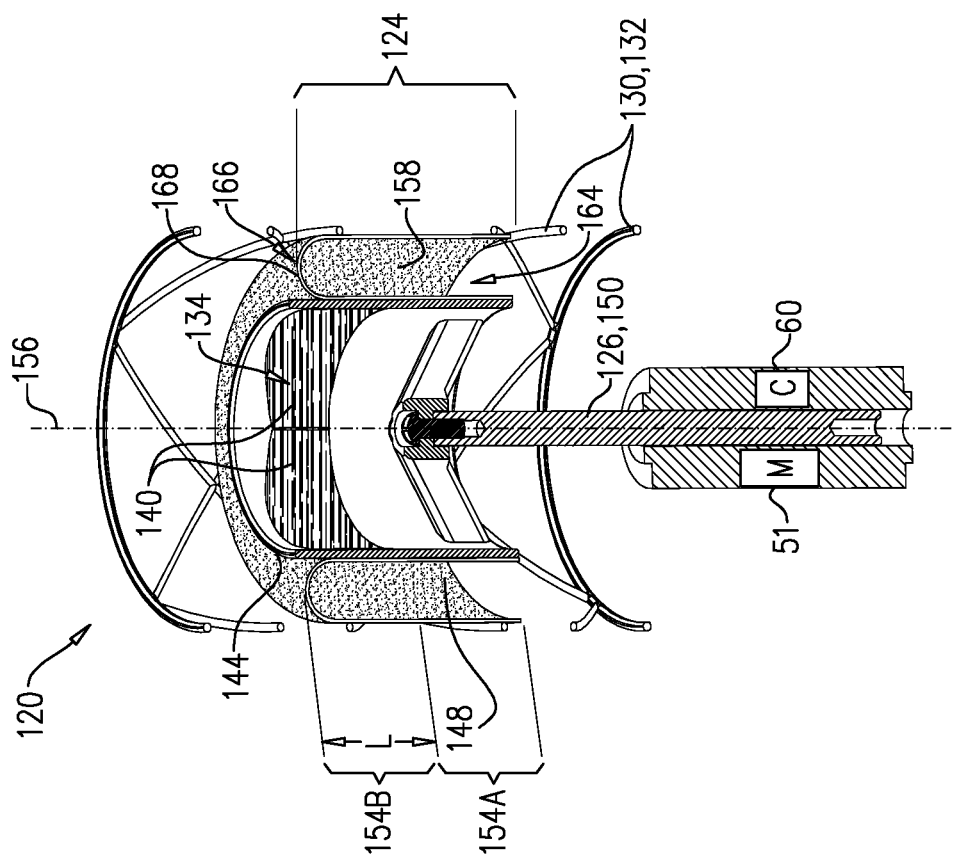
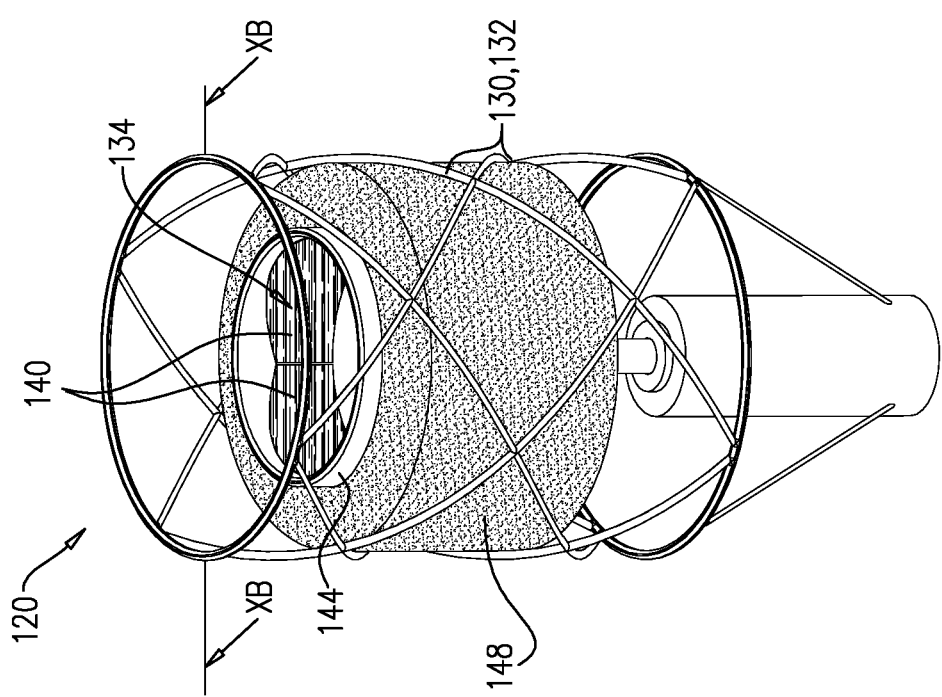

RECIPROCATING INTRAVASCULAR BLOOD PUMP

CROSS-REFERENCE TO RELATED APPLICATIONS

The present application is a continuation-in-part of U.S. application Ser. No. 15/831,973, filed Dec. 5, 2017, now U.S. Pat. No. 10,568,999, which is assigned to the assignee of the present application and incorporated herein by reference.

FIELD OF THE INVENTION

Some applications of the invention relate generally to medical procedures and implantable devices. More specifically, some applications of the invention relate to the use of a mechanical device for deployment in the circulatory system.

BACKGROUND

Cardiovascular disease is one of the leading causes of death. Blood pumps for insertion into the vasculature of a patient have been developed to provide mechanical circulatory support by supplementing the blood pumping action of a damaged or diseased heart. An example of an intravascular blood pump is the intra-aortic balloon pump, which is a pneumatic device typically deployed in an aorta of a patient to augment the pumping action of the heart. Typically, the aortic balloon pump includes a balloon, which inflates and deflates in a predetermined synchronous pattern with respect to the diastole and systole of the patient (inflates during diastole and deflates during systole). The aortic balloon pump typically inflates during diastole, thereby increasing coronary flow in the coronary arteries, and deflates during systole, thereby increasing blood flow forward in the aorta.

SUMMARY OF THE APPLICATION

In accordance with some applications of the present invention, apparatus is provided for deployment in a lumen of a blood vessel of a subject. The apparatus typically affects blood flow in the blood vessel and improves circulation.

In accordance with some applications of the present invention, the apparatus comprises a reciprocating device, which moves downstream and upstream in the blood vessel in a reciprocating pattern to provide a first effective surface area when the apparatus moves downstream and a second effective surface area when the apparatus moves upstream. Typically, when the reciprocating device assumes the first effective surface area, blood is pushed downstream in the blood vessel during downstream motion of the reciprocating device. Typically, the first effective surface area is larger for pushing blood in the blood vessel than the second effective surface area.

For some applications, the apparatus comprises a pump portion comprising an anchor and a reciprocating valve. The anchor is configured to engage a wall of the blood vessel in order to maintain the apparatus in place within the blood vessel, and the reciprocating valve is coupled to the anchor and comprising a set of one or more leaflets. The apparatus further comprises a valve driver configured to drive the reciprocating valve in a reciprocating pattern between (i) a first state in which the leaflets are in an open configuration allowing blood flow through the reciprocating valve, and (ii) a second state in which the leaflets are in a closed configuration inhibiting blood flow through the reciprocating valve. During upstream motion of the reciprocating valve, when the leaflets are in the first state, the motion of the reciprocating valve has a relatively small effect on blood flow. During downstream motion of the reciprocating valve, when the leaflets are in the second state, the motion of the reciprocating valve has a substantial effect on blood flow, driving blood in a downstream direction in the aorta.

In accordance with some applications of the present invention, the reciprocating valve comprises a cylindrical housing to which the set of one or more leaflets is coupled such that the leaflets in the second state inhibit the blood flow through the cylindrical housing. The valve driver is configured to drive the cylindrical housing to move axially with respect to the anchor in the reciprocating pattern.

For some applications, the anchor comprises a generally cylindrical stent, and the pump portion further comprises a blood-proof membrane that is fixed to the stent and to the cylindrical housing so as to (a) inhibit blood flow between the cylindrical housing and the stent and (b) allow axial movement of the cylindrical housing with respect to the stent.

There is therefore provided, in accordance with an Inventive Concept 1 of the present invention, apparatus configured to be deployed in a lumen of a blood vessel of a subject, the apparatus including:
- a pump portion including:
  - an anchor configured to engage a wall of the blood vessel in order to maintain the apparatus in place within the blood vessel; and
  - a reciprocating valve coupled to the anchor and including a set of one or more leaflets; and
- a valve driver configured to drive the reciprocating valve in a reciprocating pattern between:
  - (i) a first state in which the leaflets are in an open configuration allowing blood flow through the reciprocating valve, and
  - (ii) a second state in which the leaflets are in a closed configuration inhibiting blood flow through the reciprocating valve.

Inventive Concept 2. The apparatus according to Inventive Concept 1, wherein the blood vessel is an aorta of the subject, and wherein the apparatus is configured to be deployed in the aorta.

Inventive Concept 3. The apparatus according to Inventive Concept 1, wherein the blood vessel is a vena cava of the subject, and wherein the apparatus is configured to be deployed in the vena cava.

inventive Concept 4. The apparatus according to Inventive Concept 1, wherein the valve driver includes a rod (a) configured to be disposed parallel to a longitudinal axis of the blood vessel and downstream of the reciprocating valve when the apparatus is deployed in the blood vessel, and (b) configured to push the reciprocating valve upstream in the blood vessel in the first state, and to pull the reciprocating valve downstream in the blood vessel in the second state.

Inventive Concept 5. The apparatus according to Inventive Concept 1, wherein the valve driver is configured to axially move the reciprocating valve upstream in the first state, and to axially move the reciprocating valve downstream in the second state.

Inventive Concept 6. The apparatus according to Inventive Concept 5, wherein the valve driver includes a rod (a) disposed parallel to a longitudinal axis of pump portion 124, and (b) configured to move the reciprocating valve upstream in the first state and downstream in the second state.

Inventive Concept 7. The apparatus according to Inventive Concept 6, wherein the rod is (a) disposed downstream of the reciprocating valve, and (b) configured to push the reciprocating valve upstream in the first state, and to pull the reciprocating valve downstream in the second state.

Inventive Concept 8. The apparatus according to Inventive Concept 6, wherein the rod is (a) disposed upstream of the reciprocating valve, and (b) configured to pull the reciprocating valve upstream in the first state, and to push the reciprocating valve downstream in the second state.

Inventive Concept 9. The apparatus according to Inventive Concept 1, wherein the apparatus does not include any leaflets for allowing and inhibiting blood flow in the blood vessel in addition to the set of one or more leaflets of the reciprocating valve.

Inventive Concept 10, The apparatus according to Inventive Concept 1, wherein the apparatus does not include any leaflets that are configured to (a) open when the set of one or more leaflets of the reciprocating valve are in the closed configuration and (b) close when the set of one or more leaflets of the reciprocating valve are in the open configuration.

Inventive Concept 11. The apparatus according to Inventive Concept 1, wherein the valve driver includes a diametric magnet.

Inventive Concept 12. The apparatus according to Inventive Concept 1, wherein the valve driver includes a traverse roll.

Inventive Concept 13. The apparatus according to any one of Inventive Concepts 1-12,
wherein the reciprocating valve includes a cylindrical housing to which the set of one or more leaflets is coupled such that the leaflets in the second state inhibit the blood flow through the cylindrical housing, and
wherein the valve driver is configured to drive the cylindrical housing to move axially with respect to the anchor in the reciprocating pattern.

Inventive Concept 14. The apparatus according to Inventive Concept 13,
wherein the anchor includes a generally cylindrical stent, and
wherein the pump portion further includes a blood-proof membrane that is fixed to the stent and to the cylindrical housing so as to (a) inhibit blood flow between the cylindrical housing and the stent and (b) allow axial movement of the cylindrical housing with respect to the stent.

Inventive Concept 15. The apparatus according to Inventive Concept 14, wherein the blood-proof membrane is fixed to an external surface of the cylindrical housing.

Inventive Concept 16, The apparatus according to Inventive Concept 15,
wherein the valve driver is configured to axially move the cylindrical housing upstream in the first state, and to axially move the cylindrical housing downstream in the second state, and
wherein the blood-proof membrane is fixed to a downstream portion of the external surface of the cylindrical housing and is not fixed to an upstream portion of the external surface of the cylindrical housing, the upstream portion having an axial length, measured along a central longitudinal axis of the cylindrical housing, of at least 5 mm.

Inventive Concept 17. The apparatus according to Inventive Concept 14, wherein the blood-proof membrane, the cylindrical housing, and the stent are arranged such that a degree of invagination of the blood-proof membrane changes during axial movement of the cylindrical housing with respect to the anchor.

Inventive Concept 18. The apparatus according to Inventive Concept 17,
wherein the valve driver is configured to axially move the cylindrical housing upstream in the first state, and to axially move the cylindrical housing downstream in the second state, and
wherein the blood-proof membrane, the cylindrical housing, and the stent are arranged such that the degree of invagination of the blood-proof membrane increases during downstream movement of the cylindrical housing and decreases during upstream movement of the cylindrical housing.

Inventive Concept 19. The apparatus according to Inventive Concept 17,
wherein the valve driver is configured to axially move the cylindrical housing upstream in the first state, and to axially move the cylindrical housing downstream in the second state,
wherein the blood-proof membrane, the cylindrical housing, and the stent are arranged such that the blood-proof membrane is shaped so as to define an annular chamber between at least a portion of an external surface of the cylindrical housing and at least a portion of an inner surface of the generally cylindrical stent, and
wherein the annular chamber has an open downstream end and a closed upstream end defined by a curved portion of the blood-proof membrane.

Inventive Concept 20. The apparatus according to Inventive Concept 13,
wherein the valve driver is configured to axially move the cylindrical housing upstream in the first state, and to axially move the cylindrical housing downstream in the second state, and
wherein the valve driver is configured to drive the cylindrical housing to move axially between 10 and 20 mm in each of an upstream direction and a downstream direction during an entire cycle of the reciprocating pattern.

Inventive Concept 21. The apparatus according to Inventive Concept 13, wherein the valve driver is configured to axially move the cylindrical housing downstream in the second state, such that the reciprocating valve pushes blood at a rate of between 10 and 20 cc per second.

Inventive Concept 22. The apparatus according to Inventive Concept 13, wherein the valve driver is configured to axially move the cylindrical housing downstream in the second state, such that the reciprocating valve pushes between 10 and 20 cc during an entire operating cycle of the reciprocating pattern.

Inventive Concept 23. The apparatus according to any one of Inventive Concepts 1-12, wherein the valve driver is configured to drive the valve in the reciprocating pattern at a frequency of 1-5 Hz.

Inventive Concept 24. The apparatus according to Inventive Concept 23, wherein the valve driver is configured to drive the reciprocating valve in the reciprocating pattern at a frequency of 2-5 Hz.

Inventive Concept 25. The apparatus according to any one of Inventive Concepts 1-12, wherein the valve driver is configured to drive the valve in the reciprocating pattern at a frequency that is higher than that of a beating heart.

Inventive Concept 26. The apparatus according to any one of Inventive Concepts 1-12, wherein the reciprocating valve has a thickness of 20-200 microns.

Inventive Concept 27. The apparatus according to any one of Inventive Concepts 1-12, wherein the reciprocating valve include a material selected from the group consisting of: polyurethane or polyethylene.

Inventive Concept 28. The apparatus according to any one of Inventive Concepts 1-12, wherein the set of one or more leaflets includes 2-6 leaflets.

Inventive Concept 29. The apparatus according to any one of Inventive Concepts 1-12, wherein the anchor includes a generally cylindrical stent.

Inventive Concept 30. The apparatus according to any one of Inventive Concepts 1-12, wherein the set of one or more leaflets is less flexible than the reciprocating valve.

Inventive Concept 31. The apparatus according to any one of Inventive Concepts 1-12, wherein the set of one or more leaflets each have a thickness that is greater than a thickness of the reciprocating valve.

Inventive Concept 32. The apparatus according to any one of Inventive Concepts 1-12,
wherein the set of one or more leaflets are each shaped to define (a) a near side that is coupled to the reciprocating valve and (b) a far side, and
wherein the far side has a thickness that is greater than a thickness of the near side.

Inventive Concept 33. The apparatus according to any one of Inventive Concepts 1-12, wherein the anchor includes an O-ring anchor having an outer diameter of 15-30 mm.

Inventive Concept 34. The apparatus according to any one of Inventive Concepts 1-12, wherein the anchor is a first anchor and wherein the apparatus further includes a second anchor downstream to the first anchor.

Inventive Concept 35. The apparatus according to any one of Inventive Concepts 1-12, wherein the apparatus is not configured to coordinate the reciprocating pattern with a cardiac cycle of the subject.

Inventive Concept 36. The apparatus according to any one of Inventive Concepts 1-12, wherein the apparatus does not include any sensor of heart rate or cardiac cycle.

Inventive Concept 37. The apparatus according to any one of Inventive Concepts 1-12, wherein the leaflets include a material selected from the group consisting of: polyurethane or polyethylene.

Inventive Concept 38. The apparatus according to any one of Inventive Concepts 1-12, wherein the leaflets include animal tissue.

There is further provided, in accordance with an Inventive Concept 39 of the present invention, a method including:
deploying in a lumen of a blood vessel of a subject, in a location that is downstream of a native aortic valve of a heart of the subject, a reciprocating valve including a set of one or more leaflets; and
activating a valve driver to drive the reciprocating valve in a reciprocating pattern between:
(i) a first state in which the leaflets are in an open configuration allowing blood flow through the reciprocating valve, and
(ii) a second state in which the leaflets are in a closed configuration inhibiting blood flow through the reciprocating valve.

Inventive Concept 40. The method according to Inventive Concept 39, wherein deploying the reciprocating valve in the blood vessel includes deploying the reciprocating valve in a descending aorta.

Inventive Concept 41. The method according to Inventive Concept 39, wherein deploying the reciprocating valve in the blood vessel includes anchoring the reciprocating valve to the blood vessel using an anchor configured to engage a wall of the blood vessel.

Inventive Concept 42. The method according to inventive Concept 41, wherein the anchor includes a generally cylindrical stent.

Inventive Concept 43. The method according to Inventive Concept 41,
wherein the reciprocating valve includes a cylindrical housing to which the set of one or more leaflets is coupled such that the leaflets in the second state inhibit the blood flow through the cylindrical housing, and
wherein activating the valve driver includes activating the valve driver to drive the cylindrical housing to move axially with respect to the anchor in the reciprocating pattern.

Inventive Concept 44. The method according to Inventive Concept 43,
wherein deploying the reciprocating valve in the blood vessel includes anchoring the reciprocating valve to the blood vessel using a generally cylindrical stent configured to engage a wall of the blood vessel, and
wherein a blood-proof membrane is fixed to the stent and to an external surface of the cylindrical housing so as to (a) inhibit blood flow between the cylindrical housing and the stent and (b) allow axial movement of the cylindrical housing with respect to the stent.

Inventive Concept 45. The method according to Inventive Concept 44, wherein the blood-proof membrane is fixed to an external surface of the cylindrical housing.

Inventive Concept 46. The method according to Inventive Concept 45,
wherein activating the valve driver includes activating the valve driver to axially move the cylindrical housing upstream in the first state, and to axially move the cylindrical housing downstream in the second state, and
wherein the blood-proof membrane, the cylindrical housing and the stent are arranged such that a degree of invagination of the blood-proof membrane increases during downstream movement of the cylindrical housing and decreases during upstream movement of the cylindrical housing.

Inventive Concept 47. The method according to Inventive Concept 45,
wherein activating the valve driver includes activating the valve driver to axially move the cylindrical housing upstream in the first state, and to axially move the cylindrical housing downstream in the second state, and
wherein the blood-proof membrane is fixed to a downstream portion of the external surface of the cylindrical housing and is not fixed to an upstream portion of the external surface of the cylindrical housing, the upstream portion having an axial length, measured along a central longitudinal axis of the cylindrical housing, of at least 5 mm.

Inventive Concept 48. The method according to Inventive Concept 44, wherein the blood-proof membrane, the cylindrical housing, and the stent are arranged such that a degree of invagination of the blood-proof membrane changes during axial movement of the cylindrical housing with respect to the anchor.

Inventive Concept 49. The method according to Inventive Concept 48,
wherein activating the valve driver includes activating the valve driver to axially move the cylindrical housing upstream in the first state, and to axially move the cylindrical housing downstream in the second state, and
wherein the blood-proof membrane, the cylindrical housing, and the stent are arranged such that the degree of invagination of the blood-proof membrane increases during downstream movement of the cylindrical housing and decreases during upstream movement of the cylindrical housing.

Inventive Concept 50. The method according to Inventive Concept 48,
wherein activating the valve driver includes activating the valve driver to axially move the cylindrical housing upstream in the first state, and to axially move the cylindrical housing downstream in the second state,
wherein the blood-proof membrane, the cylindrical housing, and the stent are arranged such that the blood-proof membrane is shaped so as to define an annular chamber between at least a portion of an external surface of the cylindrical housing and at least a portion of an inner surface of the generally cylindrical stent, and
wherein the annular chamber has an open downstream end and a closed upstream end defined by a curved portion of the blood-proof membrane.

Inventive Concept 51. The method according to Inventive Concept 39, wherein activating the valve driver includes activating the valve driver to (a) axially move the reciprocating valve upstream in the blood vessel in the first state, and (b) axially move the reciprocating valve downstream in the blood vessel in the second state.

Inventive Concept 52. The method according to Inventive Concept 51, wherein activating the valve driver includes activating the valve driver to drive a rod: (a) to move the reciprocating valve upstream in the blood vessel in the first state and downstream in the blood vessel in the second state.

Inventive Concept 53. The method according to Inventive Concept 52, wherein activating the valve driver includes activating the valve driver to drive the rod: (a) to push the reciprocating valve upstream in the blood vessel in the first state, and (b) to pull the reciprocating valve downstream in the blood vessel in the second state.

Inventive Concept 54. The method according to Inventive Concept 52, wherein activating the valve driver includes activating the valve driver to drive the rod: (a) to pull the reciprocating valve upstream in the blood vessel in the first state, and (b) to push the reciprocating valve downstream in the blood vessel in the second state.

Inventive Concept 55. The method according to Inventive Concept 39, wherein the method further includes not deploying any leaflets for allowing and inhibiting blood flow in the blood vessel in addition to the set of one or more leaflets of the reciprocating valve.

Inventive Concept 56. The method according to inventive Concept 39, wherein activating the valve driver includes activating the valve driver to drive a rod: (a) to push the reciprocating valve upstream in the blood vessel in the first state, and (b) to pull the reciprocating valve downstream in the blood vessel in the second state.

Inventive Concept 57. The method according to Inventive Concept 56, wherein activating the valve driver to drive the rod includes activating the valve driver to drive the rod using a traverse roll mechanism.

Inventive Concept 58. The method according to inventive Concept 39, wherein activating the valve driver does not include activating the valve driver to coordinate the reciprocating pattern with a cardiac cycle of the subject.

Inventive Concept 59. The method according to inventive Concept 39, wherein the method does not include internally or externally coupling to the subject any sensor of heart rate or cardiac cycle.

There is further provided, in accordance with an Inventive Concept 60 of the present invention, apparatus configured to be deployed in a lumen of a blood vessel of a subject, the apparatus including:
a reciprocating device configured to move downstream and upstream in the blood vessel in a reciprocating pattern to provide:
a first effective surface area of the device for pushing blood downstream in the blood vessel during downstream motion of the reciprocating device, and
a second effective surface area of the device during upstream motion of the reciprocating device; the first effective surface area being larger for pushing blood in the blood vessel than the second effective surface area; and
a device driver configured to drive the reciprocating device in the reciprocating patter Inventive Concept 61. The apparatus according to Inventive Concept 60, wherein the reciprocating device includes a flexible membrane.

The present invention will be more fully understood from the following detailed description of applications thereof, taken together with the drawings, in which:

BRIEF DESCRIPTION OF THE DRAWINGS

FIG. 1A is a schematic illustration of apparatus for deployment in a lumen of a blood vessel of a subject being deployed in the lumen, in accordance with some applications of the present invention;

FIGS. 1B and 1C are schematic illustrations of the apparatus being operated in the lumen of the blood vessel in a first state in which blood is allowed to flow through the apparatus (FIG. 1B), and a second state in which blood is inhibited from flowing through the apparatus (FIG. 1C), in accordance with some applications of the present invention;

FIGS. 2A and 2B are schematic illustrations of additional views of the apparatus in the first and second states, in accordance with some applications of the present invention;

FIGS. 3A and 3B are schematic illustrations of a top view of the apparatus in the first and second states, in accordance with some applications of the present invention;

FIGS. 5A and 5B are schematic illustrations of cross sections of the apparatus in the first and second states, and a power source for powering the apparatus, in accordance with some applications of the present invention;

FIGS. 10A-B are schematic side and cross-sectional views, respectively, of the apparatus of FIGS. 8A and 8B in a first state in which leaflets are in an open configuration, in accordance with some applications of the present invention;

DETAILED DESCRIPTION OF APPLICATIONS

Figure 4B:
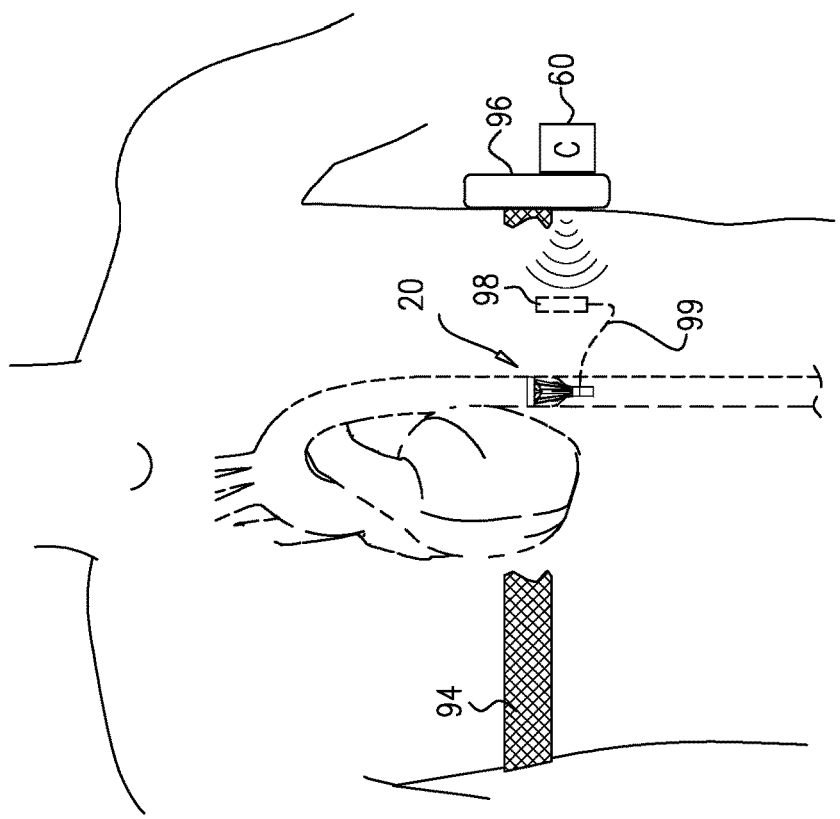
FIGS. 4A and 4B are schematic illustrations of the apparatus in the first and second states, and coupled to a power source for powering the apparatus, in accordance with some applications of the present invention.

Reference is first made to FIGS. 1A-C, which are schematic illustrations of apparatus 20 advanced and subsequently deployed in a lumen of a blood vessel 90 of a subject, in accordance with some applications of the present invention. Typically, apparatus 20 is advanced in the lumen of blood vessel 90 in a minimally-invasive procedure. Apparatus 20 is then deployed in a desired location in the blood vessel to facilitate blood flow in the blood vessel, as described hereinbelow. For example, apparatus 20 may be advanced in a delivery tool, e.g., a catheter 92, through a femoral artery in a retrograde direction and along the aorta until a desired location downstream of a native aortic valve is reached. Apparatus 20 is then deployed in the desired location in the aorta to improve blood flow in the aorta. As shown in FIG. 1A, apparatus 20 is advanced in a retrograde direction in the aorta in a collapsed configuration. Upon reaching the desired location in the aorta (e.g., in the descending aorta), apparatus 20 begins operation, as illustrated in FIGS. 1B-C. (Typically, apparatus 20 is not implanted too close to the aortic valve, such that the blood pressure stored in the aortic wall between the aortic valve and apparatus 20 during systole is sufficient to provide blood flow to the coronary arteries during diastole)

As shown in FIGS. 1B-C, for some applications, apparatus 20 comprises a pump portion 24 comprising an anchor 30 which engages a wall of blood vessel 90 in order to maintain apparatus 20 in place within blood vessel 90. Anchor 30 typically comprises an O-ring anchor having an outer diameter D1 of 15-30 mm, e.g., 20-30 mm.

Pump portion 24 further comprises a reciprocating device, e.g., reciprocating valve 34, coupled to anchor 30 and comprising (e.g., shaped to define) a set of one or more leaflets 40, e.g., 2-6 leaflets 40. It is noted that for some applications, leaflets 40 are not shown to scale and may be larger in size than as shown in FIGS. 1B-C. When leaflets 40 are in an open configuration (for example as shown in FIG. 1B), reciprocating valve 34 is shaped to define one or more windows 42 in place of where leaflets 40 are positioned in reciprocating valve 34 when leaflets 40 are in a closed configuration (for example as shown in FIG. 1C). It is noted that for some applications, windows 42 are not shown to scale and may be larger in size than as shown in the figures.

Typically, reciprocating valve 34 is a thin and flexible valve (e.g., a membrane) having a thickness T1 of 20-200 microns, e.g., 100-200 microns. Reciprocating valve 34 typically comprises a flexible material facilitating the reciprocating motion of reciprocating valve 34, and due to its thinness, minimizing development of tension and compression in the flexible material during motion of reciprocating valve 34. For example, reciprocating valve 34 may comprise a biocompatible synthetic material, e.g., polyurethane or polyethylene. For other applications, reciprocating valve 34 comprises a flexible, thin animal tissue.

For some applications, reciprocating valve 34 may be similar to a known commercial valve, such as the Edwards Sapien™ valve, *mutatis mutandis*.

In contrast, leaflets 40 are typically less flexible than reciprocating valve 34, and have a thickness that is greater than the thickness of reciprocating valve 34. Leaflets 40 are typically thicker and less flexible than reciprocating valve 34 in order to allow leaflets 40 to transition properly between open and closed configurations as described hereinbelow, and maintain a suitable seal with windows 42 of reciprocating valve 34. For some applications, leaflets 40 comprise animal tissue, e.g., porcine pericardium, which is typically a relatively thick membrane (e.g., on the order of 1-2 mm). Alternatively, leaflets 40 comprise a biocompatible synthetic material such as polyurethane or polyethylene.

Apparatus 20 further comprises a valve driver 50 configured to drive reciprocating valve 34 in a reciprocating pattern between a first state, shown in FIGS. 1B and 2A, in which leaflets 40 are in an open configuration, and a second state shown in FIG. 1C and 2B, in which leaflets 40 are in a closed configuration. Typically, valve driver 50 comprises a motor 51, which is shown highly schematically in FIGS. 2A and 2B. For example, motor 51 may comprise a linear motor. For example, a housing 53 in which the motor is disposed may be coated, e.g., with polytetrafluoroethylene (PTFE).

Typically, in the first state when leaflets 40 are in an open configuration, blood is allowed to flow through reciprocating valve 34. In the second state, when leaflets 40 are in the closed configuration, blood is typically inhibited from flowing through reciprocating valve 34. Valve driver 50 is typically configured to move (e.g., push) reciprocating valve 34 upstream in blood vessel 90 in the first state (shown in FIG. 1B), causing opening of leaflets 40 and allowing blood flow through reciprocating valve 34 in a downstream direction in blood vessel 90. Valve driver 50 is typically configured to move (e.g., pull) reciprocating valve 34 downstream in blood vessel 90 in the second state (shown in FIG. 1C), causing closing of leaflets 40 and inhibiting blood flow through reciprocating valve 34 in a downstream direction in blood vessel 90. In the transition between the first state (FIG. 1B) and the second state (FIG. 1C), the motion of reciprocating valve 34 being moved (e.g., pulled) downstream by reciprocating valve driver 50 pushes blood downstream in blood vessel 90, thereby affecting blood flow in blood vessel 90.

Typically, in the second state in which reciprocating valve 34 is moved (e.g., pulled) downstream and leaflets 40 are in the closed configuration, reciprocating valve 34 assumes a first effective surface area of reciprocating valve 34 for pushing blood downstream in blood vessel 90, due to the orientation of the leaflets. In the first state in which reciprocating valve 34 is moved (e.g., pushed) upstream and leaflets 40 are in the open configuration, reciprocating valve 34 assumes a second effective surface area of reciprocating valve 34 (having a relatively small effect on blood flow). The first effective surface area is typically larger than the second effective surface area, and has a substantial effect on blood flow, driving blood in a downstream direction in the aorta by pushing the blood.

For some applications, valve driver 50 comprises a rod 26 configured to be disposed parallel to a longitudinal axis of the blood vessel (and, typically, to a longitudinal axis of pump portion 24) and downstream of reciprocating valve 34 when apparatus 20 is deployed in blood vessel 90. Rod 26 moves (e.g., pushes) reciprocating valve 34 upstream in the blood vessel in the first state, and moves (e.g., pulls) reciprocating valve 34 downstream in blood vessel 90 in the second state. Typically, but not necessarily, reciprocating valve 34 assumes a convex configuration (as viewed from upstream of reciprocating valve 34) when rod 26 moves (e.g., pushes) reciprocating valve 34 upstream in blood vessel 90 in the first state, and a concave configuration when rod 26 moves (e.g., pulls) reciprocating valve 34 downstream in blood vessel 90 in the second state. Alternatively, rod 26 is disposed upstream of reciprocating valve 34, and rod 26 pulls reciprocating valve 34 upstream in the blood vessel in the first state, and pushes reciprocating valve 34 downstream in blood vessel 90 in the second state (configuration not shown).

Reciprocating valve 34 typically affects blood flow in blood vessel 90 by reciprocation between the first state in which rod 26 moves (e.g., pushes) reciprocating valve 34 upstream and leaflets 40 are in the open configuration, and the second state, in which rod 26 moves (e.g., pulls) reciprocating valve 34 downstream and the leaflets are in the closed configuration. The reciprocating motion of reciprocating valve 34 typically pushes the blood downstream in blood vessel 90, thereby assisting functioning of the heart. For example, apparatus 20 may be deployed in an aorta of the subject in a location that is downstream of a native aortic valve of the subject, e.g., in a descending aorta of the subject (although it is noted that apparatus 20 may be deployed in the aorta in a location that is closer to the native aortic valve, or elsewhere in the circulatory system). Operating apparatus 20 in the aorta typically increases blood flow in the aorta and reduces pressure in the ascending aorta (upstream of reciprocating valve 34).

Apparatus 20 typically comprises control circuitry 60 that is configured to control the reciprocating motion of reciprocating valve 34. Typically, apparatus 20 is not operated in coordination with a cardiac cycle of the subject. Typically, apparatus 20 is not configured to coordinate the reciprocating pattern with a cardiac cycle of the subject. Thus, apparatus 20 typically does not comprise any heart rate or cardiac cycle sensor (such as an electrode for sensing the heart rate or the cardiac cycle). For example, the reciprocating motion of reciprocating valve 34 (moving (e.g., pushing) of reciprocating valve 34 upstream and moving (e.g., pulling of reciprocating valve 34 downstream) is typically not dependent on the frequency of heart beats, and reciprocating valve 34 is typically not operated in a synchronous pattern with respect to the diastole and systole of the subject. Typically, apparatus 20 is operated such that the reciprocating motion of reciprocating valve 34 is at a frequency that is higher than that of a beating heart. For example, apparatus 20 operates at a reciprocating frequency of 1-5 Hz, e.g., 2-5 Hz. For some applications, apparatus 20 is configured to operate at a reciprocating frequency that is adjustable only by an external user interface.

It is noted that FIGS. 1A-C show blood vessel 90 as the aorta and apparatus 20 is shown in the aorta by way of illustration and not limitation. For some applications, apparatus 20 is deployed in another blood vessel 90, e.g., a vena cava of the subject.

Reference is now made to FIGS. 2A-B, which are schematic illustrations of additional views of apparatus 20, in accordance with some applications of the present invention. FIGS. 2A shows a side view of apparatus 20 in the first state in which leaflets 40 are in the open configuration, and FIG. 2B shows a side view of apparatus 20 in the second state in which leaflets 40 are in the closed configuration.

It is noted that apparatus 20 typically does not comprise any leaflets that are configured to (a) open when the set of one or more leaflets 40 of reciprocating valve 34 are in the closed configuration and (b) close when the set of one or more leaflets 40 of reciprocating valve 34 are in the open configuration. Indeed, apparatus 20 typically does not comprise any leaflets for allowing and inhibiting blood flow in the blood vessel, in addition to the set of one or more leaflets 40 of reciprocating valve 34.

For some applications, apparatus 20 comprises a second anchor 31 positioned downstream of anchor 30 and configured to engage the wall of blood vessel 90 to anchor apparatus 20 to the wall of blood vessel 90. For some applications, second anchor 31 comprises a plurality of ribs 32, e.g., 2-6 ribs 32.

For some applications, apparatus 20 additionally comprises a plurality of self-expandable support members 38 extending from a base portion 80 of apparatus 20 to anchor 30. Support members 38 are typically shaped so that apparatus 20 is retrievable. For some applications, support members 38 are arranged in the form of a stent (and not as shown in the figures).

Reference is now made to FIGS. 3A-B, which are top views of apparatus 20, in accordance with some applications of the present invention. FIG. 3A shows a top view of apparatus 20 in the first state with leaflets 40 in the open configuration and wrapped around rod 26, allowing blood flow through reciprocating valve 34. FIG. 3B shows a top view of apparatus 20 in the second state in which leaflets 40 are in the closed configuration and blood is inhibited from flowing through reciprocating valve 34.

Figure 4A:
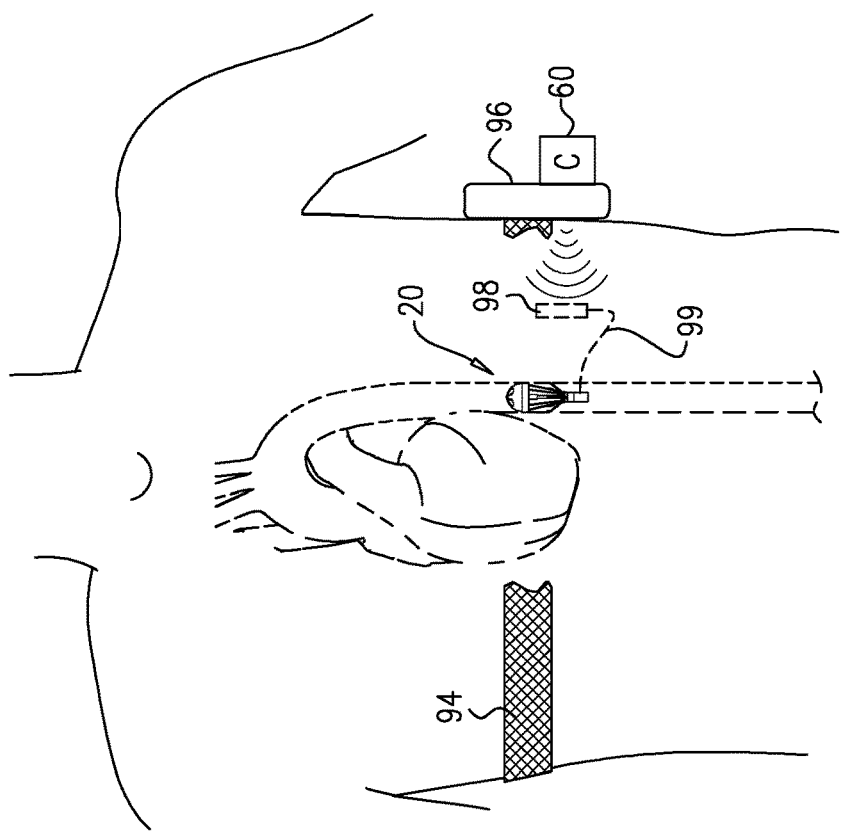

Reference is now made to FIGS. 4A-B, which are schematic illustrations of apparatus 20 in the first state (FIG. 4A) and in the second state (FIG. 4B). FIGS. 4A-B additionally show a power source for powering valve driver 50, for driving reciprocating valve 34. For some applications, apparatus 20 is powered by a radiofrequency (RF)-based system illustrated in FIGS. 4A-B. For such applications, at least one transmitter coil 96 is disposed outside the subject's body, and at least one receiver coil 98 is implanted in the subject. Transmitter coil 96 typically generates power of 3 kHz-14 MHz, e.g., 6-8 MHz or 13-14 MHz.

As shown in FIGS. 4A-B, external RF transmitter coil 96 is coupled to the subject (e.g., by a chest-band 94). RF transmitter coil 96 induces current in RF receiver coil 98 which is typically implanted subcutaneously in the subject. Power is typically carried through a wire 99 from receiver coil 98 to motor 51 of valve driver 50 (shown schematically in FIGS. 2A and 2B) in apparatus 20. Valve driver 50 in turn drives rod 26 in an upstream and downstream direction to move (e.g., push and pull) reciprocating valve 34 upstream and downstream in the blood vessel.

For some applications, valve driver 50 comprises control circuitry 60 (such as shown highly schematically in FIGS. 2A-B). For other applications, an external unit is provided that comprises control circuitry 60, which is electrically coupled to transmitter coil 96 (such as shown highly schematically in FIGS. 4A-B); in this configuration, control circuitry 60 controls the operation of valve driver 50 via the parameters of the power transmitted to receiver coil 98.

Reference is now made to FIGS. 5A-B, which are cross sections of apparatus 20, in accordance with some applications of the present invention. FIG. 5A shows a cross section of apparatus 20 in the first state with leaflets 40 in the open configuration and wrapped around rod 26, allowing blood flow through reciprocating valve 34. FIG. 5B shows a cross section of apparatus 20 in the second state in which leaflets 40 are in the closed configuration and blood is inhibited from flowing through reciprocating valve 34.

For some applications, valve driver 50 comprises a diametric magnet 55, which causes rotation of longitudinal element 36 which drives rod 26 in an upstream and downstream direction in blood vessel 90. For some applications, rod 26 is reciprocally driven by a traverse roll mechanism 46 operating between longitudinal element 36 and rod 26. Additionally, or alternatively, an extracorporeal rotating magnet 510 drives intracorporeal diametric magnet 55 to rotate, thus rotating longitudinal element 36 and driving rod 26 upstream and downstream in blood vessel 90.

Reference is now made to FIGS. 1A-C, 2A-B, 3A-B and 5A-B. Anchor 30 is shown in the drawings as a ring anchor (e.g., an O-ring) by way of illustration and not limitation. For some applications, apparatus 20 is maintained in place in blood vessel 90 by an alternative type of anchor. For example, apparatus 20 may be anchored to a wall of blood vessel 90 by a soft porous material, e.g., a suitable gauze, which at first absorbs blood but over time becomes less soft and generally impermeable to blood due to clotting of the blood therein.

Figure 6A:
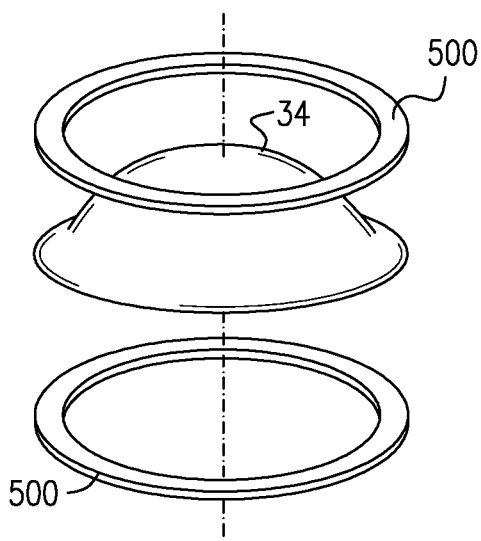
FIGS. 6A, 6B, and 6C are schematic illustrations of a reciprocating valve, in accordance with some applications of the present invention.
Figure 6B:
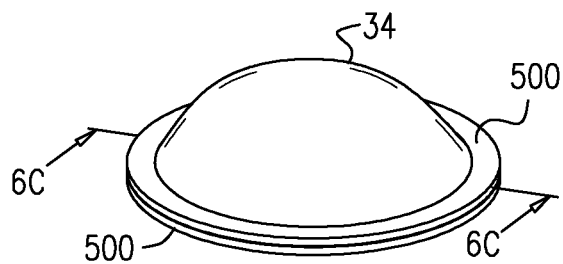
Figure 6C:
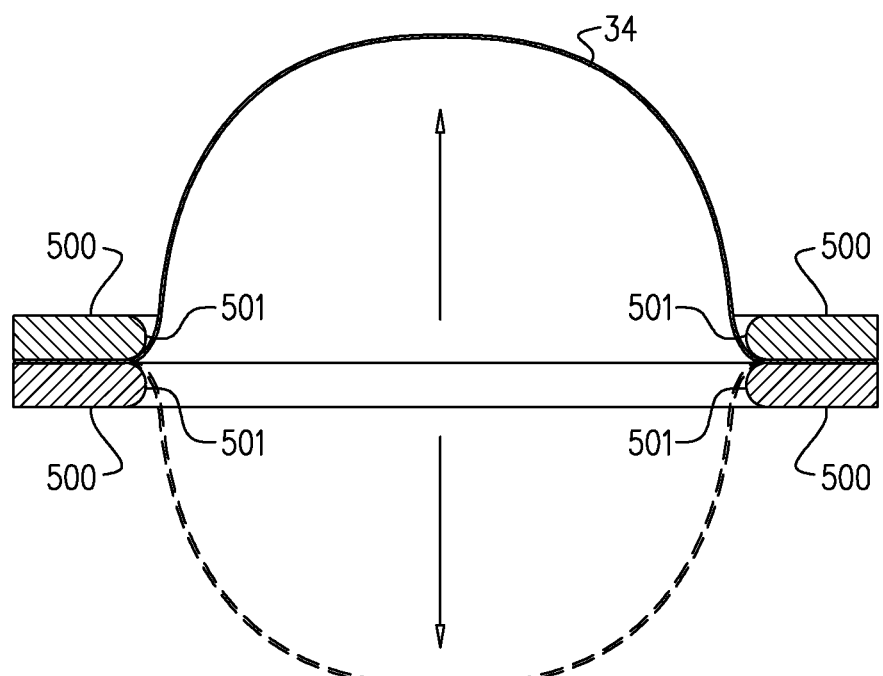

Reference is now made to FIGS. 6A-C, which are schematic illustrations of reciprocating valve 34 in accordance with some applications of the present invention. Typically, reciprocating valve 34 is clamped between two toroidal plates, e.g., washers 500, such that the edge along the perimeter of reciprocating valve 34 is compressed between washers 500. Typically, washers 500 comprise silicone, or another suitable, resilient material (which is typically slightly flexible, but may alternatively be rigid). Clamping reciprocating valve 34 between washers 500 typically secures reciprocating valve 34 and facilitates anchoring of reciprocating valve 34 to anchor 30. As shown in the cross section in FIG. 6C, each washer 500 is shaped to define a rounded inner edge 501 in order to reduce any damage to reciprocating valve 34 during the reciprocating motion of reciprocating valve 34. (Leaflets 40 and windows 42 are not shown in FIGS. 6A-C.)

Figure 7:
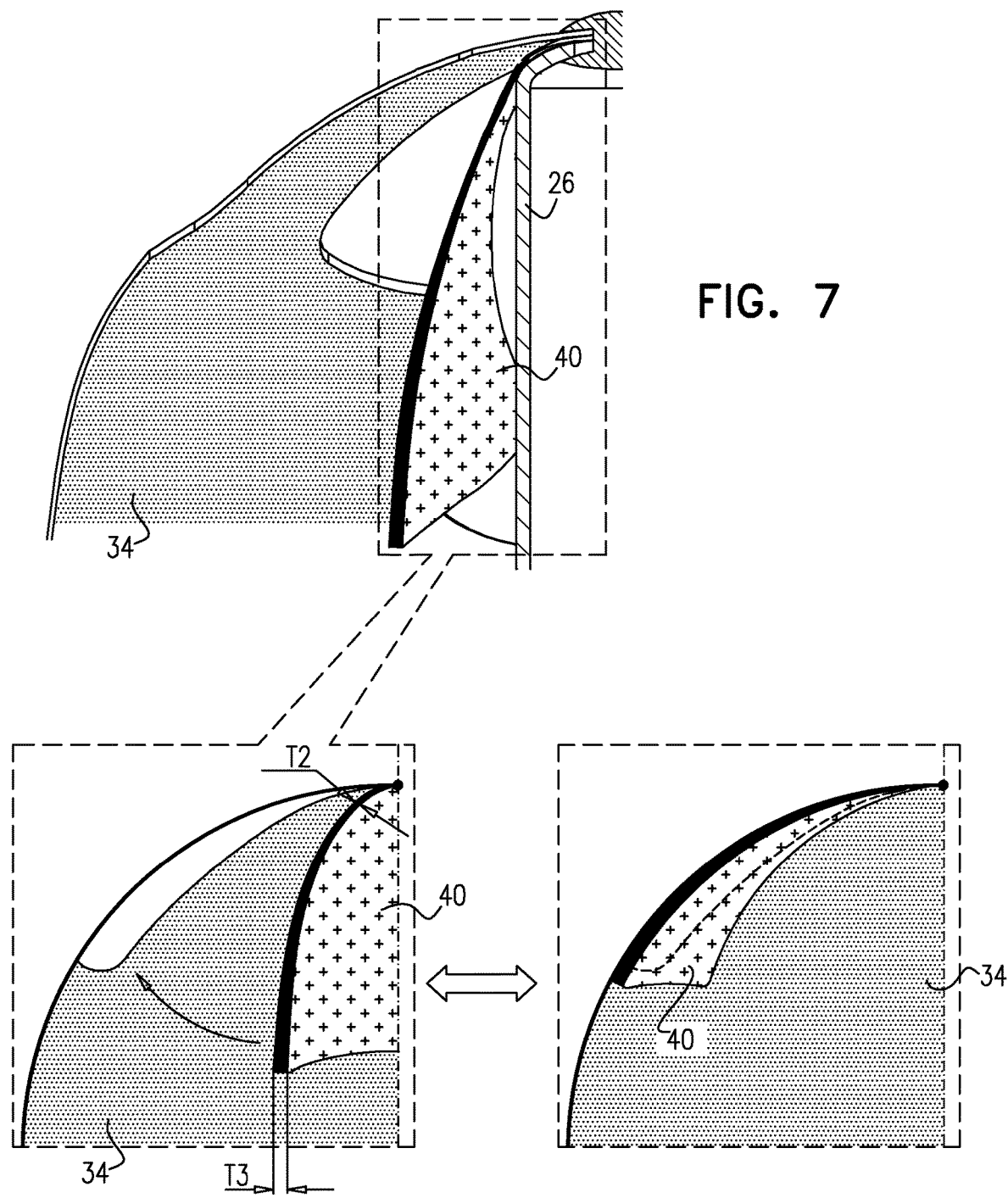
FIG. 7 is a schematic illustration of leaflets of the apparatus, in accordance with some applications of the present invention.

Reference is now made to FIG. 7, which is a schematic illustration of leaflets 40 in accordance with some applications of the present invention. As described hereinabove with reference to FIGS. 1B-C, the overall thickness of leaflets 40 is greater than that of reciprocating valve 34. Additionally, for some applications, the thickness of leaflet 40 in a near side of the leaflet (the near side being the side that is coupled to reciprocating valve 34) is less than a thickness of the leaflet at a far side of the leaflet (the far side being the side of the leaflet that is farther away from the coupling point of the leaflet with reciprocating valve 34). Typically, the thickness of leaflet 40 increases as it extends away from the coupling point between reciprocating valve 34 and leaflet 40. As shown in FIG. 7, leaflet 40 has a first thickness T2 at, or near, the coupling point with reciprocating valve 34. As leaflet 40 extends away from the coupling point with reciprocating valve 34, the thickness thereof increases gradually to a thickness T3. Leaflet 40 is typically thinner at the coupling point with reciprocating valve 34 in order to provide the leaflet with greater flexibility at the coupling point, to allow for easy motion of leaflets 40 at the coupling point. The increased thickness T3 of leaflets 40 facilitates proper placement of leaflets 40 against windows 42.

Figure 8A:
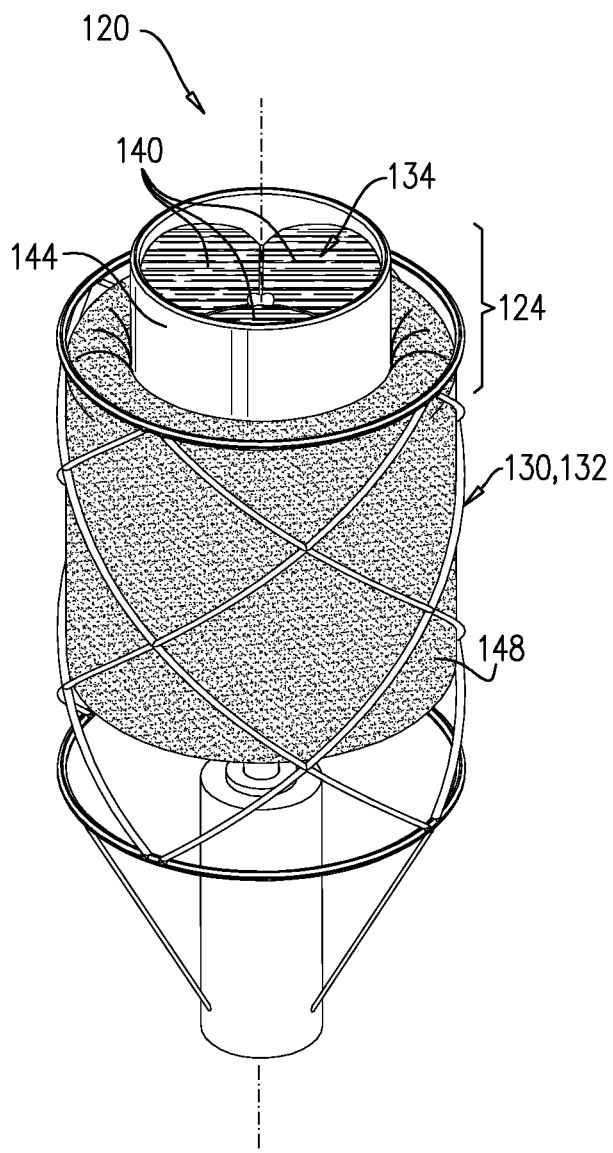
FIGS. 8A and 8B are schematic illustrations of another apparatus for deployment in a lumen of blood vessel of a subject, in accordance with some applications of the present invention.
Figure 8B:
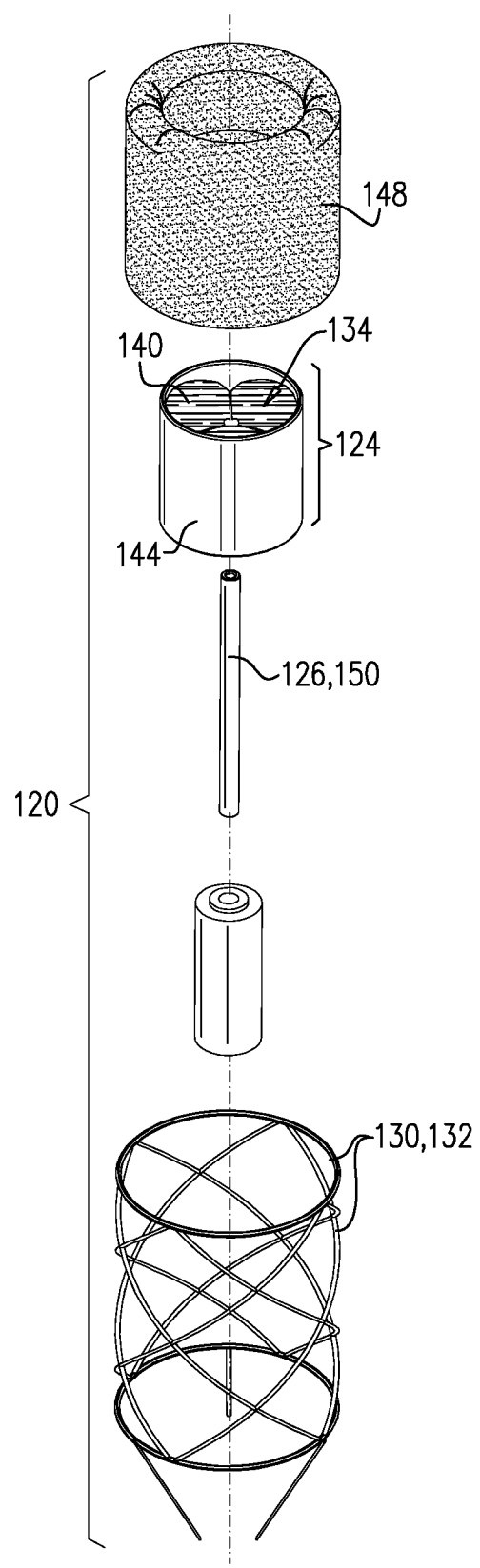

Reference is now made to FIGS. 8A and 8B, which are schematic illustrations of apparatus 120 for deployment in a lumen of blood vessel 90 of a subject, in accordance with some applications of the present invention. FIG. 8A shows apparatus 120 fully assembled, and FIG. 8B shows an exploded view of the elements of apparatus 120. Other than as described hereinbelow, apparatus 120 is generally similar to apparatus 20, described hereinabove with reference to FIGS. 1A-7, and may implement any of the techniques thereof, including deployment techniques, *mutatis mutandis*, and like reference numerals refer to like elements.

Figure 9B:
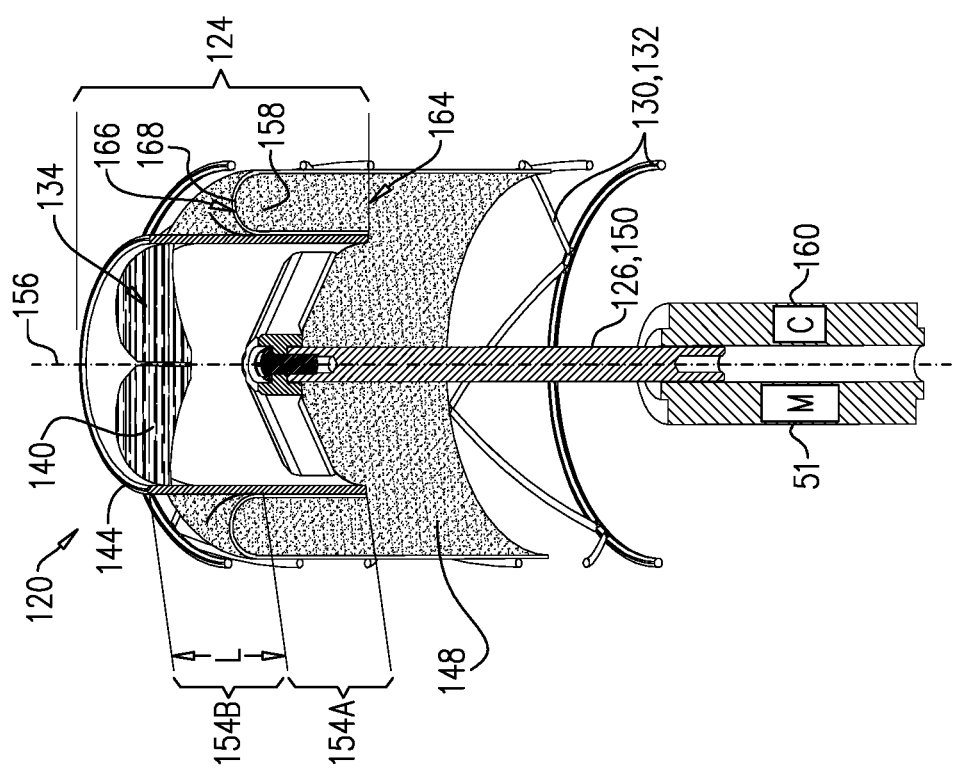
FIGS. 9A-B are schematic side and cross-sectional views, respectively, of the apparatus of FIGS. 8A and 8B in a second state in which leaflets are in a closed configuration, in accordance with some applications of the present invention.
Figure 9A:
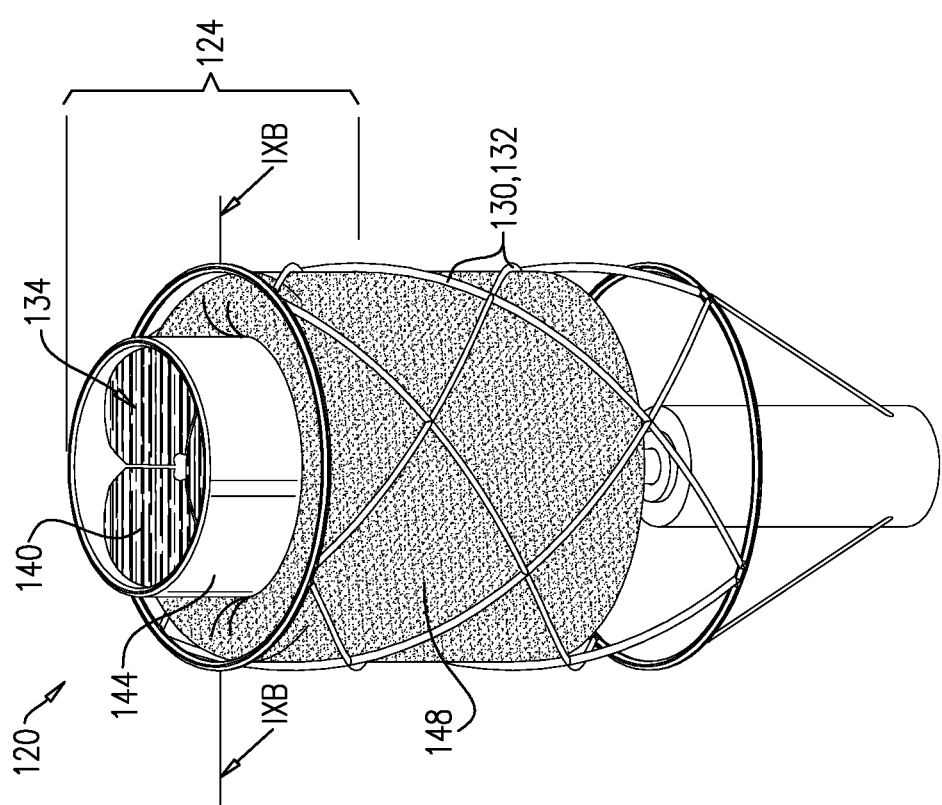

Reference is further made to FIGS. 9A-B, which are schematic side and cross-sectional views, respectively, of apparatus 120 in the second state in which leaflets 140 are in the closed configuration, in accordance with some applications of the present invention. Reference is still further made to FIGS. 10A-B, which are schematic side and cross-sectional views, respectively, of apparatus 120 in the first state in which leaflets 140 are in the open configuration, in accordance with some applications of the present invention.

Apparatus 120 comprises a pump portion 124 comprising an anchor 130 which engages a wall of blood vessel 90 in order to maintain apparatus 120 in place within blood vessel 90. For some applications, anchor 130 comprises a generally cylindrical stent 132. For example, stent 132 may have an outer diameter D1 of 15-30 mm, e.g., 20-30 mm.

Pump portion 124 further comprises a reciprocating valve 134, coupled to anchor 130 and comprising (e.g., shaped to define) a set of one or more leaflets 140, e.g., 2-6 leaflets 140. For some applications, reciprocating valve 134 may be similar to a known commercial valve, such as the Edwards Sapien™ valve, *mutatis mutandis*.

Apparatus 120 further comprises a valve driver 150 configured to drive reciprocating valve 134 in a reciprocating pattern between a first state, shown in FIGS. 10A-B, in which leaflets 140 are in an open configuration, and a second state shown in FIGS. 8A-B and 9A-B, in which leaflets 140 are in a closed configuration. Typically, in the first state when leaflets 140 are in an open configuration, blood is allowed to flow through reciprocating valve 134. In the second state, when leaflets 140 are in the closed configuration, blood is typically inhibited from flowing through reciprocating valve 134.

Valve driver 150 may implement any of the techniques of valve driver 50 described hereinabove. For example, for some applications, valve driver 150 comprises control circuitry 60 (such as shown highly schematically in FIGS. 9B and 10B). For other applications, an external unit is provided that comprises control circuitry 60. Control circuitry 60 is described hereinabove.

For some applications, valve driver 150 comprises a rod 126 configured to be disposed parallel to a longitudinal axis of the blood vessel (and, typically, to a longitudinal axis of pump portion 124) and downstream of reciprocating valve 134 when apparatus 120 is deployed in blood vessel 90. Rod 126 moves (e.g., pushes) reciprocating valve 134 upstream in the blood vessel in the first state, and moves (e.g., pulls) reciprocating valve 134 downstream in blood vessel 90 in the second state. Alternatively, rod 126 is disposed upstream of reciprocating valve 134, and rod 126 pulls reciprocating valve 134 upstream in the blood vessel in the first state, and pushes reciprocating valve 134 downstream in blood vessel 90 in the second state (configuration not shown).

As described in more detail hereinbelow with reference to FIG. 12, reciprocating valve 134 typically affects blood flow in blood vessel 90 by reciprocation between the first state in which rod 126 moves (e.g., pushes) reciprocating valve 134 upstream and leaflets 140 are in the open configuration, and the second state, in which rod 126 moves (e.g., pulls) reciprocating valve 134 downstream and the leaflets are in the closed configuration.

Typically, reciprocating valve 134 comprises a cylindrical housing 144 to which the set of one or more leaflets 140 is coupled such that leaflets 140 in the second state inhibit the blood flow through cylindrical housing 144. For example, leaflets 140 may be coupled to an internal surface of cylindrical housing 144. Cylindrical housing 144 may be elliptical (e.g., circular, as shown), or may have another shape. Valve driver 150 is configured to drive cylindrical housing 144 to move axially with respect to anchor 130 in the reciprocating pattern.

For some applications, pump portion 124 further comprises a blood-proof membrane 148 that is fixed to stent 132 and to cylindrical housing 144 so as to (a) inhibit blood flow between cylindrical housing 144 and stent 132 and (b) allow axial movement of cylindrical housing 144 with respect to stent 132. Blood-proof membrane 148 may be fixed to an external surface 152 of cylindrical housing 144 (as shown), an internal surface of cylindrical housing 144, and/or an end surface of cylindrical housing 144.

Optionally, blood-proof membrane 148 comprises a polymer (such as polyurethane), latex, silicone, or a fabric.

For some applications, elements of apparatus 120 have one or more of the following dimensions:
  cylindrical housing 144—an axial length of between 10 and 25 mm, such as between 12 and 20 mm, e.g., 15 mm,
  cylindrical housing 144—an outer diameter of between 10 and 25 mm, such as between 12 and 20 mm, e.g., 15 mm,
  rod 126—an outer diameter of between 10 and 25 mm, such as between 12 and 20 mm, e.g., 15 mm,
  housing 53—an outer diameter of between 4 and 10 mm, such as between 5 and 8 mm, e.g., 7 mm,
  housing 53—an axial length of between 10 and 30 mm, such as between 15 and 25 mm, e.g., 20 mm,
  stent 132—an outer diameter of between 15 and 25 mm, such as 20 mm, and/or
  stent 132—an axial length of between 25 and 50 mm, such as between 30 and 40 mm.

For some applications, as labeled in FIGS. 9B and 10B, blood-proof membrane 148 is fixed to external surface 152 of cylindrical housing 144. As mentioned above, for some applications valve driver 150 is configured to axially move cylindrical housing 144 upstream in the first state, and to axially move cylindrical housing 144 downstream in the second state; in some of these applications, blood-proof membrane 148 is fixed to a downstream portion 154A of external surface 152 of cylindrical housing 144 and is not fixed to an upstream portion 154B of external surface 152 of cylindrical housing 144. For example, upstream portion 154B may have an axial length L, measured along a central longitudinal axis 156 of cylindrical housing 144, of at least 3 mm, such as at least 5 mm, e.g., at least 10 mm. Optionally, downstream portion 154A reaches a downstream end of cylindrical housing 144; further optionally, downstream portion 154A is essentially only near the downstream end of cylindrical housing 144, e.g., extends less than 1 mm upstream from the downstream end of cylindrical housing 144. Optionally, blood-proof membrane 148 is fixed to downstream portion 154A by stitching, welding, gluing, and/or squeezing (e.g., using a ring).

Similarly, blood-proof membrane 148 is fixed to an axial portion of anchor 130, e.g., stent 132, optionally using any of the techniques described in the immediately preceding paragraph.

For some applications, an axial length of a portion of blood-proof membrane 148 that touches upstream portion 154B of external surface 152 of cylindrical housing 144 varies based on the degree of invagination of blood-proof membrane 148 (i.e., how much the membrane is folded over into itself), which typically changes during axial movement of cylindrical housing 144 with respect to anchor 130, as described hereinbelow with reference to FIG. 12. (Thus, a portion of blood-proof membrane 148, even though it is not fixed to upstream portion 154B, may nevertheless sometimes touch upstream portion 154B, such as shown, for example, in FIG. 10B and other figures; the level of touching varies based on the level of invagination.)

As mentioned above, for some applications valve driver 150 is configured to axially move cylindrical housing 144 upstream in the first state, and to axially move cylindrical housing 144 downstream in the second state; in some of these applications, blood-proof membrane 148, cylindrical housing 144, and stent 132 are arranged such that blood-proof membrane 148 is shaped so as to define an annular chamber 158 between at least a portion of external surface 152 of cylindrical housing 144 and at least a portion of an inner surface 162 of generally cylindrical stent 132. (It is noted that an axial length of annular chamber 158 varies based on the degree of invagination of blood-proof membrane 148 (i.e., how much the membrane is folded over into itself), which typically changes during axial movement of cylindrical housing 144 with respect to anchor 130, as described hereinbelow with reference to FIG. 12.)

Typically, annular chamber 158 has an open downstream end 164 and a closed upstream end 166 defined by a curved portion 168 of blood-proof membrane 148. Typically, because annular chamber 158 has closed upstream end 166, valve driver 150 requires less power to move cylindrical housing 144 upstream that would be necessary if annular chamber 158 had an open upstream end.

Alternatively, blood-proof membrane 148 is arranged in an opposite direction from that shown in the figures, such that annular chamber 158 has a closed downstream end and an open upstream end defined by curved portion 168 of blood-proof membrane 148.

Figure 11:
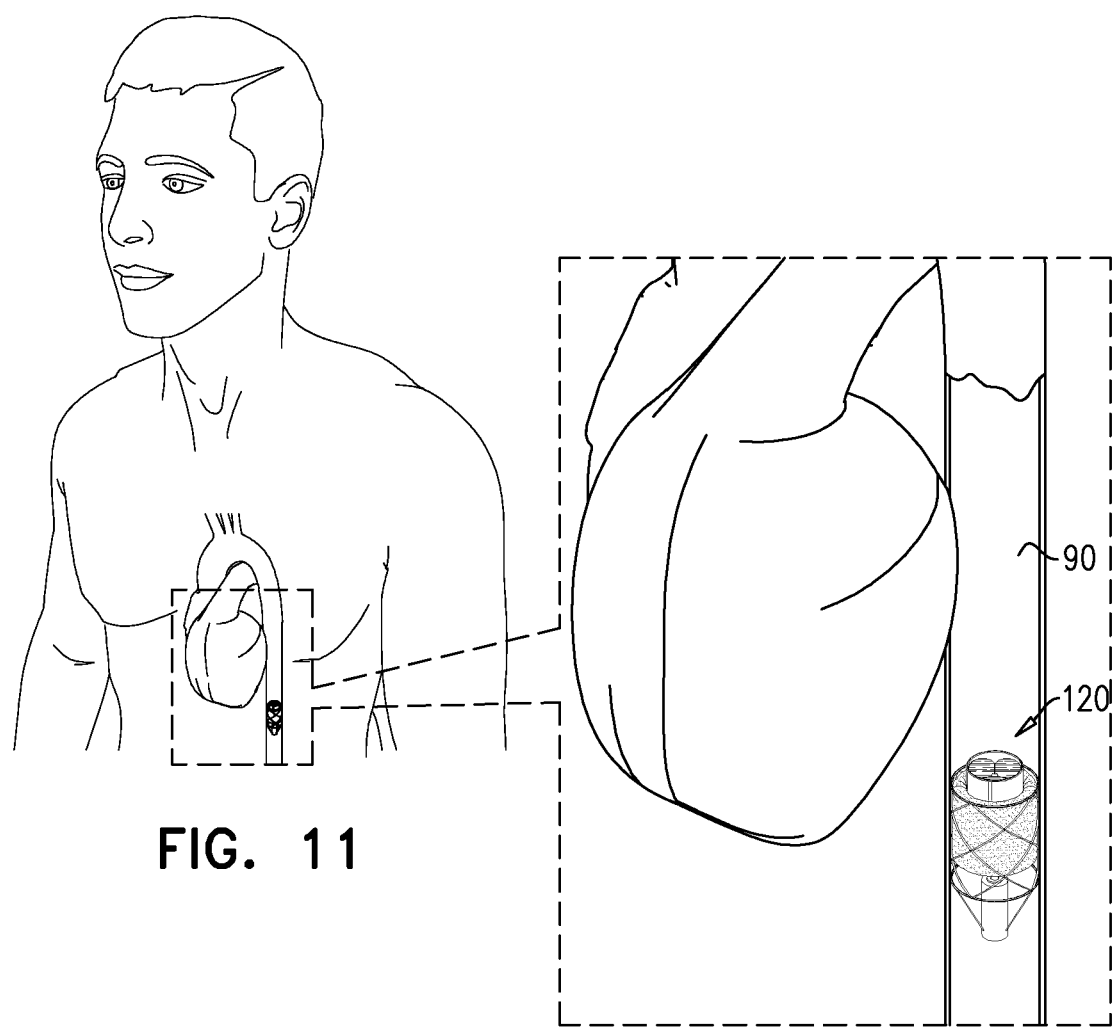
FIG. 11 is a schematic illustration of the apparatus of FIGS. 8A and 8B deployed in the lumen of the blood vessel, in accordance with some applications of the present invention.

Reference is now made to FIG. 11, which is a schematic illustration of apparatus 120 deployed in the lumen of blood vessel 90, in accordance with some applications of the present invention. Apparatus 120 may optionally implement the power transmission techniques described hereinabove for apparatus 20 with reference to FIGS. 4A-B. The reciprocating motion of reciprocating valve 134 typically pushes the blood downstream in blood vessel 90, thereby assisting functioning of the heart. For example, apparatus 120 may be deployed in an aorta of the subject in a location that is downstream of a native aortic valve of the subject, e.g., in a descending aorta of the subject (although it is noted that apparatus 120 may be deployed in the aorta in a location that is closer to the native aortic valve, or elsewhere in the circulatory system). Operating apparatus 120 in the aorta typically increases blood flow in the aorta and reduces pressure in the ascending aorta (upstream of reciprocating valve 134).

Figure 12:
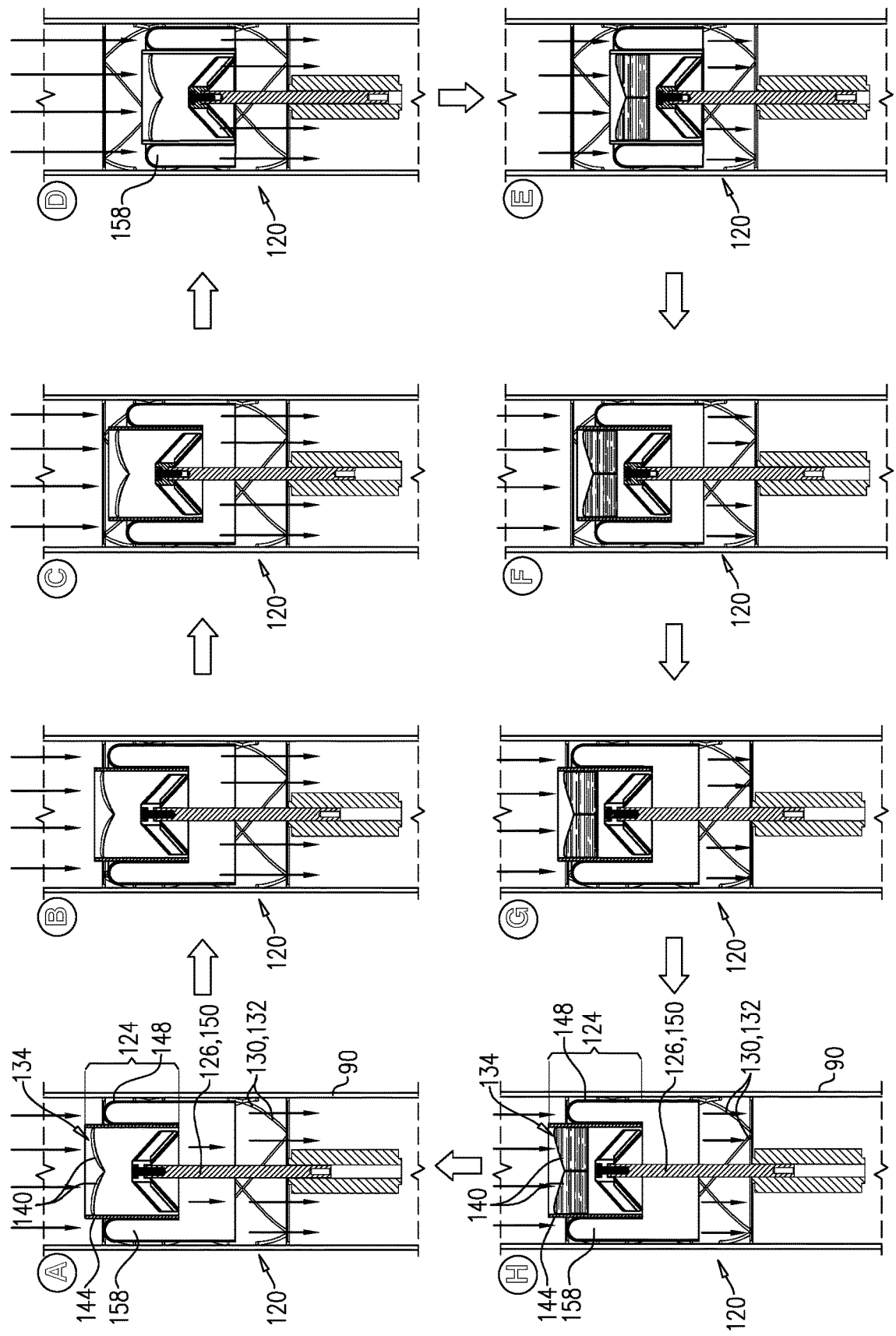
FIG. 12 is a schematic illustration of representative phases of the reciprocating pattern of the apparatus of FIGS. 8A and 8B during a single of cycle of the reciprocating pattern, in accordance with some applications of the present invention.

Reference is now made to FIG. 12, which is a schematic illustration of representative phases of the reciprocating pattern of apparatus 120 during a single of cycle of the reciprocating pattern, in accordance with some applications of the present invention.

The upper row of FIG. 12 shows apparatus 120 when reciprocating valve 134 is in the second state, in which leaflets 140 are in the closed configuration, such that blood is inhibited from flowing through reciprocating valve 134. In Stage A of the cycle of the reciprocating pattern, compression begins as valve driver 150 moves (e.g., pulls) reciprocating valve 134 downstream in blood vessel 90. Downstream movement of reciprocating valve 134 from Stage A to Stage D of the cycle of the reciprocating pattern pushes blood downstream in blood vessel 90. For some applications, this downstream movement of reciprocating valve 134 pushes blood at a rate of between 10 and 20 cc per second, such as between 15 and 20 cc per second, e.g., about 16 cc per second. Alternatively or additionally, for some applications, this downstream movement of reciprocating valve 134 pushes between 10 and 20 cc, such as between 15 and 20 cc, e.g., about 16 cc, during an entire operating cycle of the reciprocating pattern.

The lower row of FIG. 12 shows apparatus 120 when reciprocating valve 134 is in the first state, in which leaflets 140 are in the open configuration, such that blood is allowed to flow through reciprocating valve 134. As valve driver 150 begins to move (e.g., push) reciprocating valve 134 upstream in blood vessel 90 in Stage E of the cycle of the reciprocating pattern, leaflets 140 open (because of the pressure gradient across leaflets 140 created by the upstream motion of reciprocating valve 134), thereby allowing natural cardiac-driven downstream blood flow (e.g., during systole) through reciprocating valve 134 as reciprocating valve 134 moves upstream from Stage E to Stage H of the cycle of the reciprocating pattern.

It is noted that the blood flow symbolically shown in the bottom row of FIG. 12 is not caused by reciprocating valve 134; when leaflets 140 are open, reciprocating valve 134 at most interferes only minimally with natural blood flow. The lengths of the blood-flow arrows in FIG. 12 highly symbolically illustrate different flow rates; the relative lengths of the arrows should not be interpreted as representing any particular ratios of blood flow rates. In addition, as mentioned above, the reciprocating valves described herein are typically not operated in a synchronous pattern with respect to the diastole and systole of the subject. Therefore, when Stage E to Stage H of the cycle of the reciprocating pattern happen to fall at least partially during diastole, there may be no or very little blood flow during a portion of the cycle of the reciprocating pattern that happens to fall during diastole.

Upon completion of Stage H of the cycle of the reciprocating pattern, the cycle repeats as valve driver 150 begins to again move (e.g., pull) reciprocating valve 134 downstream in blood vessel 90 at Stage A of the cycle of the reciprocating pattern. As valve driver 150 begins to move (e.g., pull) reciprocating valve 134 downstream in blood vessel 90, leaflets 140 close (because of the pressure gradient across leaflets 140 created by the downstream motion of reciprocating valve 134). As a result, reciprocating valve 134 transitions back to the second state described hereinabove with reference to the upper row of FIG. 12.

For some applications, valve driver 150 is configured to axially move reciprocating valve 134 (and cylindrical housing 144) between 10 and 20 mm in each direction (downstream and upstream) during an entire cycle of the reciprocating pattern, such as between 12 and 18 mm, e.g., 15 mm.

For some applications, blood-proof membrane 148, cylindrical housing 144, and stent 132 are arranged such that a degree of invagination of blood-proof membrane 148 (i.e., how much the membrane is folded over into itself) changes during axial movement of cylindrical housing 144 with respect to anchor 130. As mentioned above, for some applications valve driver 150 is configured to axially move cylindrical housing 144 upstream in the first state, and to axially move cylindrical housing 144 downstream in the second state; in some of these applications, blood-proof membrane 148, cylindrical housing 144, and stent 132 are arranged such that the degree of invagination of blood-proof membrane 148 increases during downstream movement of cylindrical housing 144 (as shown in the upper row of FIG. 12) and decreases during upstream movement of cylindrical housing 144 (as shown in the lower row of FIG. 12).

For some applications, apparatus 120 is configured such that all implanted elements of apparatus 120 other than anchor 130 (e.g., stent 132) may be decoupled from anchor 130 after implantation and explanted, leaving anchor 130 implanted. Optionally, these explanted elements may be replaced with other similar elements by introducing these other similar elements into the body and coupling them to anchor 130.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus configured to be deployed in a lumen of a blood vessel of a subject, the apparatus comprising:
    (a) a pump portion comprising:
        (i) an anchor configured to engage a wall of the blood vessel in order to maintain the apparatus in place within the blood vessel; and
        (ii) a reciprocating valve coupled to the anchor and comprising a set of one or more leaflets; and
    (b) a valve driver configured to drive the reciprocating valve in a reciprocating pattern at a frequency of 2-5 Hz between:
        (i) a first state in which the leaflets are in an open configuration allowing blood flow through the reciprocating valve, and
        (ii) a second state in which the leaflets are in a closed configuration inhibiting blood flow through the reciprocating valve.

2. The apparatus according to claim 1, wherein the blood vessel is an aorta of the subject, and wherein the apparatus is configured to be deployed in the aorta.

3. The apparatus according to claim 1, wherein the valve driver comprises a rod (a) configured to be disposed parallel to a longitudinal axis of the blood vessel and downstream of the reciprocating valve when the apparatus is deployed in the blood vessel, and (b) configured to push the reciprocating valve upstream in the blood vessel in the first state, and to pull the reciprocating valve downstream in the blood vessel in the second state.

4. The apparatus according to claim 1, wherein the valve driver is configured to axially move the reciprocating valve upstream in the first state, and to axially move the reciprocating valve downstream in the second state.

5. The apparatus according to claim 4, wherein the valve driver comprises a rod (a) disposed parallel to a longitudinal axis of the pump portion, and (b) configured to move the reciprocating valve upstream in the first state and downstream in the second state.

6. The apparatus according to claim 5, wherein the rod is (a) disposed downstream of the reciprocating valve, and (b) configured to push the reciprocating valve upstream in the first state, and to pull the reciprocating valve downstream in the second state.

7. The apparatus according to claim 1, wherein the apparatus does not comprise any leaflets for allowing and inhibiting blood flow in the blood vessel in addition to the set of one or more leaflets of the reciprocating valve.

8. The apparatus according to claim 1, wherein the apparatus does not comprise any leaflets that are configured to (a) open when the set of one or more leaflets of the reciprocating valve are in the closed configuration and (b) close when the set of one or more leaflets of the reciprocating valve are in the open configuration.

9. The apparatus according to claim 1,
wherein the reciprocating valve comprises a cylindrical housing to which the set of one or more leaflets is coupled such that the leaflets in the second state inhibit the blood flow through the cylindrical housing, and
wherein the valve driver is configured to drive the cylindrical housing to move axially with respect to the anchor in the reciprocating pattern.

10. The apparatus according to claim 9,
wherein the valve driver is configured to axially move the cylindrical housing upstream in the first state, and to axially move the cylindrical housing downstream in the second state, and
wherein the valve driver is configured to drive the cylindrical housing to move axially between 10 and 20 mm in each of an upstream direction and a downstream direction during an entire cycle of the reciprocating pattern.

11. The apparatus according to claim 9, wherein the valve driver is configured to axially move the cylindrical housing downstream in the second state, such that the reciprocating valve pushes blood at a rate of between 10 and 20 cc per second.

12. The apparatus according to claim 9, wherein the valve driver is configured to axially move the cylindrical housing downstream in the second state, such that the reciprocating valve pushes between 10 and 20 cc during an entire operating cycle of the reciprocating pattern.

13. The apparatus according to claim 1, wherein the apparatus is not configured to coordinate the reciprocating pattern with a cardiac cycle of the subject.

14. The apparatus according to claim 1, wherein the apparatus does not comprise any sensor of heart rate or cardiac cycle.

15. Apparatus configured to be deployed in a lumen of a blood vessel of a subject, the apparatus comprising:
(a) a pump portion comprising:
(i) an anchor configured to engage a wall of the blood vessel in order to maintain the apparatus in place within the blood vessel; and
(ii) a reciprocating valve coupled to the anchor and comprising a set of one or more leaflets; and
(b) a valve driver configured to drive the reciprocating valve in a reciprocating pattern between:
(i) a first state in which the leaflets are in an open configuration allowing blood flow through the reciprocating valve, and
(ii) a second state in which the leaflets are in a closed configuration inhibiting blood flow through the reciprocating valve,
wherein the reciprocating valve comprises a cylindrical housing to which the set of one or more leaflets is coupled such that the leaflets in the second state inhibit the blood flow through the cylindrical housing,
wherein the valve driver is configured to drive the cylindrical housing to move axially with respect to the anchor in the reciprocating pattern,
wherein the anchor comprises a generally cylindrical stent, and
wherein the pump portion further comprises a blood-proof membrane that is fixed to the stent and to the cylindrical housing so as to (a) inhibit blood flow between the cylindrical housing and the stent and (b) allow axial movement of the cylindrical housing with respect to the stent.

16. The apparatus according to claim 15, wherein the blood-proof membrane is fixed to an external surface of the cylindrical housing.

17. The apparatus according to claim 16,
wherein the valve driver is configured to axially move the cylindrical housing upstream in the first state, and to axially move the cylindrical housing downstream in the second state, and
wherein the blood-proof membrane is fixed to a downstream portion of the external surface of the cylindrical housing and is not fixed to an upstream portion of the external surface of the cylindrical housing, the upstream portion having an axial length, measured along a central longitudinal axis of the cylindrical housing, of at least 5 mm.

18. The apparatus according to claim 15, wherein the blood-proof membrane, the cylindrical housing, and the stent are arranged such that a degree of invagination of the blood-proof membrane changes during axial movement of the cylindrical housing with respect to the anchor.

19. The apparatus according to claim 18,
wherein the valve driver is configured to axially move the cylindrical housing upstream in the first state, and to axially move the cylindrical housing downstream in the second state, and
wherein the blood-proof membrane, the cylindrical housing, and the stent are arranged such that the degree of invagination of the blood-proof membrane increases during downstream movement of the cylindrical housing and decreases during upstream movement of the cylindrical housing.

20. The apparatus according to claim 18,
wherein the valve driver is configured to axially move the cylindrical housing upstream in the first state, and to axially move the cylindrical housing downstream in the second state,
wherein the blood-proof membrane, the cylindrical housing, and the stent are arranged such that the blood-proof membrane is shaped so as to define an annular chamber between at least a portion of an external surface of the cylindrical housing and at least a portion of an inner surface of the generally cylindrical stent, and
wherein the annular chamber has an open downstream end and a closed upstream end defined by a curved portion of the blood-proof membrane.

21. The apparatus according to claim 15, wherein the valve driver is configured to drive the reciprocating valve in the reciprocating pattern at a frequency of 2-5 Hz.

22. A method comprising:
deploying in a lumen of a blood vessel of a subject, in a location that is downstream of a native aortic valve of a heart of the subject, a reciprocating valve comprising a set of one or more leaflets; and
activating a valve driver to drive the reciprocating valve in a reciprocating pattern at a frequency of 2-5 Hz between:
  (i) a first state in which the leaflets are in an open configuration allowing blood flow through the reciprocating valve, and
  (ii) a second state in which the leaflets are in a closed configuration inhibiting blood flow through the reciprocating valve.

23. A method comprising:
deploying in a lumen of a blood vessel of a subject, in a location that is downstream of a native aortic valve of a heart of the subject, an apparatus comprising a pump portion, which comprises (a) an anchor configured to engage a wall of the blood vessel in order to maintain the apparatus in place within the blood vessel, and (b) a reciprocating valve coupled to the anchor and comprising a set of one or more leaflets; and
activating a valve driver to drive the reciprocating valve in a reciprocating pattern between:
  (i) a first state in which the leaflets are in an open configuration allowing blood flow through the reciprocating valve, and
  (ii) a second state in which the leaflets are in a closed configuration inhibiting blood flow through the reciprocating valve,
wherein the reciprocating valve comprises a cylindrical housing to which the set of one or more leaflets is coupled such that the leaflets in the second state inhibit the blood flow through the cylindrical housing,
wherein activating the valve driver to drive the reciprocating valve comprises activating the valve driver to drive the cylindrical housing to move axially with respect to the anchor in the reciprocating pattern,
wherein the anchor comprises a generally cylindrical stent, and
wherein the pump portion further comprises a blood-proof membrane that is fixed to the stent and to the cylindrical housing so as to (a) inhibit blood flow between the cylindrical housing and the stent and (b) allow axial movement of the cylindrical housing with respect to the stent.

* * * * *